US012376814B2

(12) United States Patent
Dey et al.

(10) Patent No.: US 12,376,814 B2
(45) Date of Patent: Aug. 5, 2025

(54) QUANTIFICATION OF NONCALCIFIC AND CALCIFIC VALVE TISSUE FROM CORONARY CT ANGIOGRAPHY

(71) Applicant: CEDARS-SINAI MEDICAL CENTER, Los Angeles, CA (US)

(72) Inventors: Damini Dey, Los Angeles, CA (US); Sebastien Cadet, Los Angeles, CA (US); Piotr Slomka, Los Angeles, CA (US); Rajendra Makkar, Beverly Hills, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 437 days.

(21) Appl. No.: 17/993,819

(22) Filed: Nov. 23, 2022

(65) Prior Publication Data
US 2023/0157658 A1 May 25, 2023

Related U.S. Application Data

(60) Provisional application No. 63/287,868, filed on Dec. 9, 2021, provisional application No. 63/282,853, filed on Nov. 24, 2021.

(51) Int. Cl.
*A61B 6/50* (2024.01)
*A61B 6/00* (2006.01)
(52) U.S. Cl.
CPC ............ *A61B 6/504* (2013.01); *A61B 6/5217* (2013.01)

(58) Field of Classification Search
CPC .............................. A61B 6/504; A61B 6/5217
USPC ......................................................... 382/128
See application file for complete search history.

(56) References Cited

U.S. PATENT DOCUMENTS

| | | | |
|---|---|---|---|
| 9,087,147 B1 * | 7/2015 | Fonte | A61B 5/0263 |
| 2012/0041739 A1 * | 2/2012 | Taylor | G06T 7/12 |
| | | | 382/128 |
| 2014/0378845 A1 * | 12/2014 | Nadkarni | A61B 5/0062 |
| | | | 600/478 |
| 2020/0237329 A1 * | 7/2020 | Min | G06T 7/97 |
| 2020/0327664 A1 * | 10/2020 | Wilson | G06F 18/2431 |

FOREIGN PATENT DOCUMENTS

CA              3227901 A1 *    2/2023           A61B 5/0066

* cited by examiner

*Primary Examiner* — Gabriel I Garcia
(74) *Attorney, Agent, or Firm* — NIXON PEABODY LLP

(57) ABSTRACT

Calcific and noncalcific aortic tissue components can be quantified. Pre-intervention planning computed tomography angiography imaging data is received. A region of interest is defined between the lower coronary ostium and the virtual basal ring. Cross-sectional images of the region of interest are rendered and calcific and noncalcific tissue components are identified based on Hounsfield unit thresholds. The volumes of the identified calcific and noncalcific tissue components are calculated and used to determine a total tissue volume (e.g., fibrocalcific volume) for the valve, as well as component percentages of the total tissue volume for the calcific and noncalcific components. These volumes and/or component percentages can be leveraged to predict severe AS, identify prognosis of post-TAVI outcomes, or otherwise facilitate planning of medical intervention.

27 Claims, 15 Drawing Sheets

QUANTIFICATION OF NONCALCIFIC AND CALCIFIC VALVE TISSUE FROM CORONARY CT ANGIOGRAPHY

CROSS-REFERENCE TO RELATED APPLICATIONS

The present application claims the benefit of U.S. Provisional Patent Application No. 63/282,853 filed Nov. 24, 2021 and U.S. Provisional Patent Application No. 63/287,868 filed Dec. 9, 2021, each of which are is hereby incorporated by reference in its entirety.

STATEMENT REGARDING FEDERALLY SPONSORED RESEARCH OR DEVELOPMENT

This invention was made with government support under Grant No. HL148787 RO1 awarded by National Institutes of Health. The government has certain rights in the invention.

TECHNICAL FIELD

The present disclosure relates to cardiology generally and more specifically to systems and methods for quantitatively characterizing aortic valve tissue composition and further leveraging that characterization.

BACKGROUND

Calcific aortic stenosis (AS) is a highly prevalent heart valve disorder that occurs when the heart's aortic valve narrows due to calcium deposits that build up on the aortic valve's leaflets. Transvalvular gradient is commonly used to characterize AS when patients are referred for aortic valve replacement, such as via post-transcatheter aortic valve implantation (TAVI). High transvalvular gradients in those with calcific AS results from the progression of aortic valve calcification, restrictive opening of thickened valve leaflets, and eventual obstruction of flow across the aortic valve. Among patients with low-flow low-gradient (LFLG)-AS, restricted leaflet opening is considered to result from reduced stroke volume due to increased left ventricular stiffness.

Since aortic valve replacement, such as TAVI, is a risky procedure, it is important to ascertain a patient's prognosis pre-intervention. Increased aortic valve calcium has been associated with paravalvular regurgitation, higher frequency of post-dilatation, and adverse clinical events following TAVI. However, the impact of non-calcific leaflet thickening on post-TAVI outcomes has not been characterized.

Before certain interventions, such as a TAVI procedure, pre-intervention data can be collected and used to help plan the procedure. Often, this pre-intervention data includes computed tomography (CT) angiography (CTA) imaging data. CTA imaging makes use of an injected contrast material to visualize blood flow within cardiac tissue. These images can provide a useful view of the shape and boundaries of the valve prior to an intervention. While a separate electrocardiogram-gated non-contrast cardiac computed tomography (CT) can be used to quantify aortic valve calcium in individuals for whom echocardiography is inconclusive, additional radiation exposure required by this separate CT imaging session is not desirable.

There is a need to provide improved prognoses pre-intervention for individuals suffering from calcific AS, as well as improved differentiation between AS patients suffering from high-gradient AS and LFLG-AS. There is a need to provide improved assessment of AS severity. There is a need to provide such improvements using already required imaging data, without requiring additional imaging and the concomitant radiation exposure.

SUMMARY

The term embodiment and like terms are intended to refer broadly to all of the subject matter of this disclosure and the claims below. Statements containing these terms should be understood not to limit the subject matter described herein or to limit the meaning or scope of the claims below. Embodiments of the present disclosure covered herein are defined by the claims below, supplemented by this summary. This summary is a high-level overview of various aspects of the disclosure and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this disclosure, any or all drawings and each claim.

Embodiments of the present disclosure include a method comprising receiving imaging data of a portion of a heart containing a valve. The method further includes determining a region of interest. The region of interest contains the valve. The method further includes generating cross-sectional images of the region of interest based at least in part on the determined region of interest and the received imaging data. The method further includes identifying both calcific tissue components and noncalcific tissue components within the region of interest based at least in part on the generated cross-sectional images. The method further includes calculating a calcific tissue volume based at least in part on the calcific tissue components. The method further includes calculating a noncalcific tissue volume based at least in part on the noncalcific tissue components. The method further includes calculating a total tissue volume associated with the valve based at least in part on the calcific tissue volume and the noncalcific tissue volume.

In some cases, determining the region of interest includes generating multiplanar reconstructions based at least in part on the imaging data; automatically detecting a lower coronary ostium associated with the valve using the multiplanar reconstructions; automatically detecting a virtual basal ring of the valve using the multiplanar reconstructions; and automatically defining the region of interest as bounded by the detected lower coronary ostium and the detected virtual basal ring. In some cases, determining the region of interest further includes presenting the region of interest via a display device; receiving user input indicative of one or more manual adjustments to the region of interest; and updating the region of interest based on the one or more manual adjustments.

In some cases, generating the cross-sectional images of the region of interest include rendering, based at least in part on the imaging data, serial multiplanar images orthogonal to a longitudinal axis of an ascending aorta associated with the heart. In some cases, identifying both the calcific tissue components and the noncalcific tissue components includes, for each tissue component within the region of interest: determining a Hounsfield unit value associated with the tissue component; identifying the tissue component as a calcific tissue component when the Hounsfield unit value exceeds a calcific tissue threshold value; and identifying the tissue component as a noncalcific tissue component when the Hounsfield unit value is below a non-calcific tissue threshold value. In some cases, the calcific tissue threshold value is between 600 HU and 700 HU. In some cases, the non-calcific tissue threshold value is between 300 HU and 400 HU. In some cases, the calcific tissue threshold value is 650 HU. In some cases, the non-calcific tissue threshold value is 350 HU.

In some cases, the method further comprises presenting the imaging data on a display device; and presenting, on the display device and in association with the imaging data, i) the calcific tissue volume; ii) a calcific tissue percentage of the total tissue volume; iii) the noncalcific tissue volume; iv) a noncalcific tissue percentage of the total tissue volume; v) the total tissue volume; or vi) any combination of i-v. In some cases, the method further comprises generating a severe aortic stenosis score based at least in part on the noncalcific tissue volume, wherein the severe aortic stenosis score is indicative of a severity of aortic stenosis associated with the valve.

Embodiments of the present disclosure include a system comprising one or more data processor and a non-transitory computer-readable storage medium containing instructions which, when executed on the one or more data processors, cause the one or more data processors to perform the method(s) described above.

Embodiments of the present disclosure include a computer-program product tangibly embodied in a non-transitory machine-readable storage medium, including instructions configured to cause a data processing apparatus to perform the method(s) described above.

BRIEF DESCRIPTION OF THE DRAWINGS

The specification makes reference to the following appended figures, in which use of like reference numerals in different figures is intended to illustrate like or analogous components.

DETAILED DESCRIPTION

Figure 1:
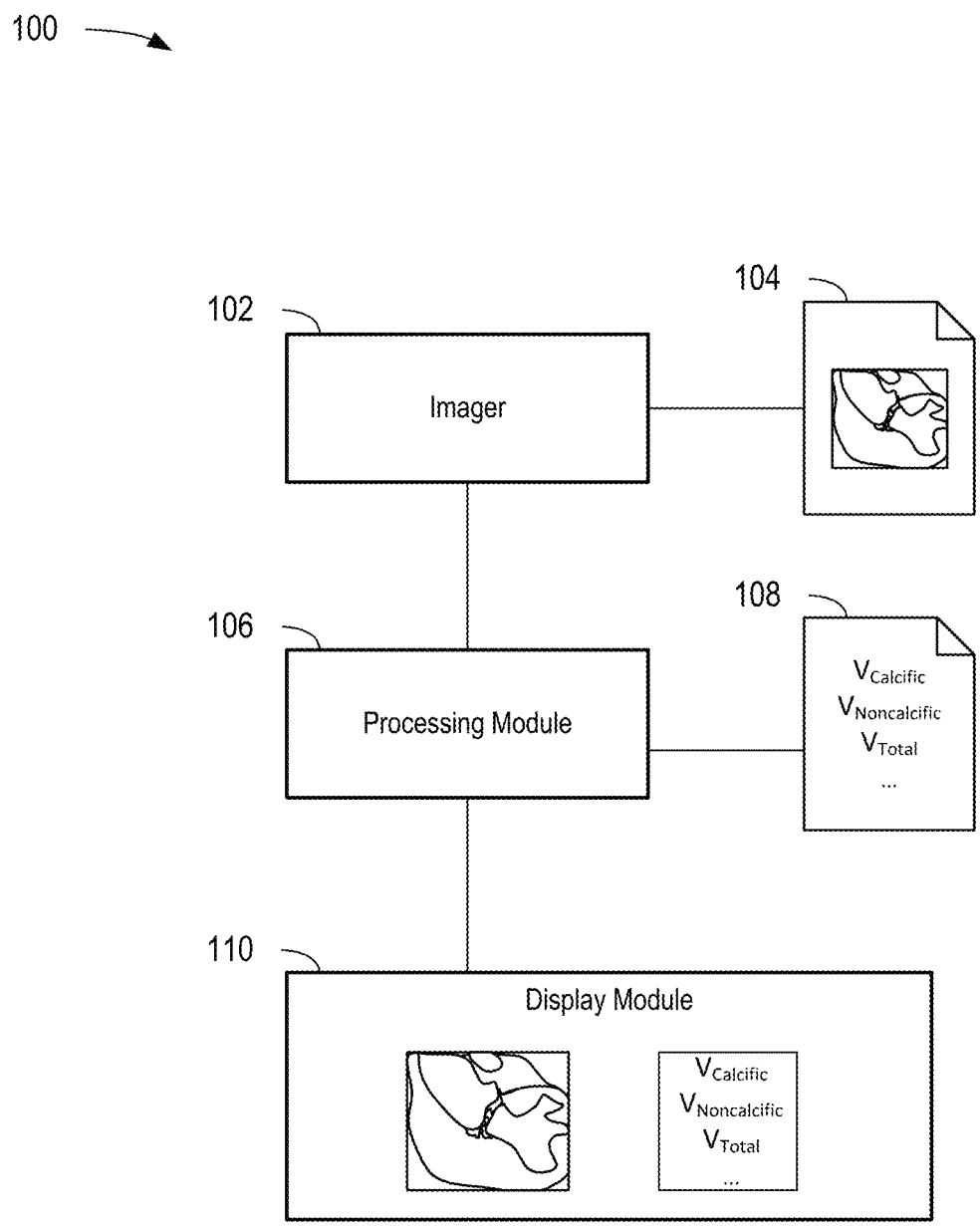
FIG. 1 is a schematic diagram depicting a computing environment for acquiring and processing imaging data, according to certain aspects of the present disclosure.

Certain aspects and features of the present disclosure relate to quantifying calcific and noncalcific aortic tissue components. Pre-intervention planning computed tomography angiography imaging data is received. A region of interest is defined between the lower coronary ostium and the virtual basal ring. Cross-sectional images of the region of interest are rendered and calcific and noncalcific tissue components are identified based on Hounsfield unit thresholds. The volumes of the identified calcific and noncalcific tissue components are calculated and used to determine a total tissue volume (e.g., fibrocalcific volume, or sum of calcific tissue volume and noncalcific tissue volume) for the valve, as well as component percentages of the total tissue volume for the calcific and noncalcific components. These volumes and/or component percentages can be leveraged to predict severe aortic stenosis (AS), identify prognosis of post-transcatheter aortic valve implantation (TAVI) outcomes, or otherwise facilitate planning of medical intervention.

In some cases, non-contrast computed tomography (CT) imaging can be used to identify aortic valve calcium, which is used to assess severe AS patients, especially those with low-flow-low-gradient (LFLG)-AS. This consideration of only calcification, however, fails to consider noncalcific tissue. While calcification is seen in nearly all stenotic aortic valves, they are often preceded by fibrotic thickening of aortic valve leaflets. While younger patients with bicuspid valves comprise the vast majority of patients with more valvular thickening compared to calcification, cases of severe stenosis in tri-leaflet aortic valves with minimal calcification are also encountered. In a number of patients with AS, valve leaflet calcification as assessed by non-contrast CT can underestimate the severity of AS.

According to certain aspects and features of the present disclosure, measurements of calcific and noncalcific tissue can be obtained from CT angiography (CTA). These measurements can be used to improve prediction of severe AS over using only aortic valve calcium scoring and can improve estimation of post-intervention outcomes. Further, the inclusion of noncalcific tissue indices into a diagnostic scheme of AS can expand the clinical utility of CTA for disease severity grading and can enable non-invasive monitoring of therapies aimed at reducing aortic valve thickening.

Generally, prior to a TAVI procedure or other such intervention, CTA imaging is collected to facilitate procedural planning of the intervention. According to certain aspects of the present disclosure, this imaging data can be used for a more complete characterization of aortic valve tissue beyond merely calcium assessment. Certain aspects of the present disclosure relate to a semi-automated or automated technique for quantitatively characterizing aortic valve tissue composition, the results of which can be useful in identifying AS severity, differentiating patients with high-gradient (HG)-AS from patients with LFLG-AS, and may provide prognostic information with respect to post-intervention outcomes. This technique makes use of CTA imaging data, thus obviating the need for additional, non-contrast CT imaging and its concomitant radiation exposure. This minimization of additional radiation exposure is especially important for individuals with diagnosed or suspected AS, since those individuals are likely to already be submitted to higher-than-usual radiation exposure due to the imaging needed to monitor, diagnose, and treat AS.

Using CTA imaging data, a region of interest can be defined around a valve. This region of interest can be automatically defined (e.g., using a machine learning algorithm trained to identify valve tissue using labeled training data), semi-automatically define, or manually defined. Semi-automatic defining of the region of interest can first automatically define, using multiplanar reconstructions, an initial region of interest between the lower coronary ostium and the virtual basal ring that is formed by the hinge points of each aortic valve cusp. Then, serial multiplanar reformatted images orthogonal to the longitudinal axis of the ascending aorta can be rendered to obtain cross-sectional images of the respective region with contouring. A series of adjustable points (e.g., 15-20 adjustable points) can be automatically applied, allowing the user flexibility to manually adjust any of the adjustable points to further define the region of interest.

After the region of interest is defined, tissue components can be identified using Hounsfield unit (HU) thresholds. Each tissue region (e.g., each voxel of the region of interest) can be analyzed to determine its HU value, which can then be compared against threshold values to determine if the tissue region is calcific or noncalcific. Any tissue regions that fall outside of the threshold values can be ignored or defined separately (e.g., defined as non-valvular tissue).

In some cases, calcific tissue can have HU values at or above a calcific HU threshold, which can be between 600-700 HU, such as 650 HU. Non-calcific tissue can have HU values at or below an upper noncalcific HU threshold, which can be between 300-400 HU, such as 350 HU. In some cases, the HU values for non-calcific tissue can also be at or above a lower noncalcific HU threshold, which can be between −50 and −10 HU, such as −30 HU.

In some cases, however, obtaining consistent attenuation thresholds (e.g., HU thresholds) for calcific and noncalcific tissue is difficult, especially due to the wide variation in contrast concentrations in the blood pool. Certain aspects and features of the present disclosure relate to automatically deriving attenuation thresholds based on Gaussian mixture modeling.

In some cases, calcific HU thresholds and noncalcific HU thresholds can be automatically determined through Gaussian mixed modeling. The Gaussian mixed model can assume three distributions, including i) blood pool tissue; ii) calcific tissue; and iii) noncalcific tissue. The result of the application of Gaussian mixed modeling is a different distribution estimating the CT attenuation (in HU) present in the region of interest for each of the blood pool tissue, the calcific tissue, and the noncalcific tissue. These distributions can be used to establish HU thresholds for calcific and noncalcific tissue, such as based on the blood pool distribution. Since the thresholds are based on relative distributions of CT attenuation in the aortic valve and surrounding blood pool observed in the imaging data, the thresholds are adaptive to any given set of imaging data.

In an example, automatically obtaining HU thresholds can include initially defining a lower threshold for non-calcific tissue (e.g., at 45 HU). A Gaussian mixture model can be applied to the HU values to establish a Gaussian distribution for the blood pool, which will fall between the noncalcific tissue (e.g., fibrosis) and the calcific tissue (e.g., calcium). The HU values can be associated with a diastolic phase (e.g., usually 70% R-R interval). Then, HU thresholds can be established based on the blood pool Gaussian distribution. More specifically, an upper noncalcific HU threshold can be established at a low end of the blood pool Gaussian distribution (e.g., at or around the lower 0.3 percentile), and a lower calcific HU threshold can be established at a high end of the blood pool Gaussian distribution (e.g., at or around the upper 99.7 percentile). To account for differences in valve size, calcific and non-calcific volumes can be indexed to the area of the valve's annulus.

Use of HU thresholds, and especially automatically generated HU thresholds (e.g., determined through Gaussian mixture modeling), permits calcific volumes, noncalcific volumes, and/or fibrocalcific volumes to be easily and rapidly calculated with little input (e.g., calculated after the user identifies the aortic valve plane and volume of interest around the valve) or no input from a user. As a result, actionable data can be obtained and presented to a user quickly, with little chance of human error, with excellent intra- and inter-observer repeatability, and with excellent scan-rescan reproducibility.

In some cases, classification of tissue as calcific or non-calcific can be manually adjusted, as needed. For example, after automatic classification, a three-dimensional model of the valve can be presented to the user with calcific components visually distinguishable from noncalcific components. In such an example, the user may be able to provide inputs to adjust the calcific/noncalcific classifications, such as by manually indicating certain tissue is calcific, noncalcific, or neither, or by manually adjusting one of more of the HU thresholds.

After classification of tissue components, a volume of calcific tissue and/or a volume of noncalcific tissue can be calculated. A total tissue volume, or fibrocalcific volume, can be calculated as the sum of the calcific and noncalcific tissue volumes. A calcific tissue percentage and/or a non-calcific tissue percentage can be calculated by dividing the volume of that particular component's volume over the total tissue volume. A fibrocalcific ratio can be calculated by dividing the calcific volume by the noncalcific volume.

Any of i) the calcific tissue volume; ii) the calcific tissue percentage of the total tissue volume; iii) the noncalcific tissue volume; iv) the noncalcific tissue percentage of the total tissue volume; v) the total tissue volume; vi) the fibrocalcific ratio; or vii) any combination of i-vi can be used as results. The results can be displayed and/or further leveraged. For example, the results can be used to determine a score (e.g., a numerical score) indicative of a patient's estimated severity of AS. In such an example, an indication of AS can be presented if the score exceeds a threshold value. In such an example, categorical indications of levels of severity of AS can be presented for different score thresholds (e.g., a score of 60-70 may indicate moderately high severity of AS, a score of 71-85 can indicate high severity of AS, and a score of 86-100 can indicate a very high severity of AS). In another example, the results can be displayed in association with the imaging data so that a user can see the imaging data that resulted in the given result (e.g., a CTA image of the heart can be presented alongside a total tissue volume, a calcific tissue percentage of the total tissue volume, and a noncalcific tissue percentage of the total tissue volume).

Certain aspects of the present disclosure permit the determination of calcific tissue volumes and/or percentages, noncalcific volumes and/or percentages, and total tissue volumes for heart valves (e.g., aortic valves) from CTA imaging data. These various values derived from the CTA imaging data have been found to be especially useful in assessing AS and estimating post-TAVI outcomes. It has been determined that total tissue volume can be a useful indicator to identify HG-AS and LFLG-AS. It has also been determined that noncalcific tissue volume and/or percentage is especially useful at distinguishing HG-AS from LFLG-AS. It has also been determined that the addition of non-calcific tissue volume and/or percentage to standard aortic valve calcium parameters (e.g., via an Agatston score) improves their predictive value for severe AS. It has also been determined that noncalcific tissue volume and/or percentage is especially useful at predicting a major adverse cardiovascular event (MACE) following TAVI.

Interestingly, histopathological analysis of debris captured with cerebral protection devices during TAVI showed different forms of non-calcific tissue and thrombus to compose the majority of the liberated material. The association of CTA-defined noncalcific tissue with stroke may be applied for a personalized approach in TAVI. One approach could employ different pre-emptive measures such as application of cerebral protection devices and/or stronger anti-thrombotic therapy following the procedure depending on the noncalcific tissue values. Alternatively, in patients with native valve presenting extremely large deposits of non-calcific tissue, in whom another precautionary steps are precluded, referral for surgical aortic valve replacement rather than TAVI could be considered.

Overall, quantitative CTA assessment of aortic valve tissue volume and composition can improve identification of severe AS, differentiation between HG and LFLG AS in patients referred for TAVI, and prediction of 30-day MACEs post-TAVI, over the current clinical standard. Inclusion of quantitative measurement of non-calcific aortic valve tissues into tomographic work-up of patients referred for TAVI may improve classification of diseased valves and the prediction of adverse outcomes.

While described herein with reference to TAVI procedures, aspects and features of the present disclosure can be used outside of the scope of TAVI procedures, such as simply to assess AS when no TAVI procedure is planned, or to help plan different procedures, such as surgical valve replacement.

Certain aspects of the present disclosure provide for an anatomic assessment describing the total burden of disease in an aortic valve, measuring both calcific and fibrotic thickening, and demonstrating a close correlation with haemodynamic aortic stenosis severity in both men and women. The fibrocalcific volume can also reveal important sex-specific differences in the pathology of aortic stenosis, highlighting the relative important of fibrosis in women, and can demonstrate strong capacity to both predict and track disease progression in patients with aortic stenosis.

The aortic valve fibrocalcific volume holds several conceptual advantages in the assessment of aortic stenosis. It provides an anatomic flow-independent measure that is not subject to fluctuations in loading conditions or stroke volume and quantifies the overall aortic valve disease burden. Unlike CT calcium scoring, it does not ignore the contribution of fibrosis to progressive aortic valve stenosis. Fibrosis is the dominant driver of disease progression for a substantial proportion of patients with aortic stenosis, and is of particular relevance to women, for whom valve fibrosis makes a larger contribution to the pathology of aortic stenosis than in men. Further, in some examples, similar correlations existed between fibrocalcific volume and disease severity in both male and female participants, with the correlation being mainly driven by the calcific volume in men and the non-calcific volume in women. In those examples, the fibrocalcific volume also appeared more closely associated with disease progression in women than measures focusing on calcium. Finally, the use of CT angiography also provides excellent spatial resolution making it much easier, as compared to CT calcium scoring, to differentiate calcific and non-calcific thickening of the aortic valve leaflets from that originating from adjacent structures. These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative embodiments but, like the illustrative embodiments, should not be used to limit the present disclosure. The elements included in the illustrations herein may not be drawn to scale.

FIG. 1 is a schematic diagram depicting a computing environment 100 for acquiring and processing imaging data, according to certain aspects of the present disclosure. The computing environment 100 can include an imager 102, a processing module 106, and a display module 110. The imager 102, processing module 106, and display module 110 can be incorporated into a single housing or split into any number of housings, whether physically coupled together or not. The imager 102, processing module 106, and display module 110 can be located in a shared location (e.g., a room, suite, facility, or building) or in different locations. In some cases, the imager 102 can be located in a first location and the processing module 106 and display module 110 can be located in a separate, second location. For example, the imager 102 can be a CT scanner located in a medical imaging facility and the processing module 106 and display module 110 can be a physician's computer workstation (e.g., the processor and display of the computer workstation) in the physician's office that is located in a separate facility, separate city, or even separate county as the medical imaging facility. Other combinations can occur.

The imager 102 can be any suitable imaging device for generating CT imaging data 104 of cardiac tissue. According to certain aspects and features of the present disclosure, the imager 102 is a CT scanner that acquires imaging data 104 in the form of CT images. The imager 102 can include an emitter (e.g., an X-ray emitter), a detector (e.g., an X-ray detector) and any other components usable to generate and/or transmit the imaging data 104 from the data acquired by the detector. The imager 102 can be used to detect radiation (e.g., X-rays) passing through a patient's tissue (e.g., cardiac tissue). As the radiation passes through different types of tissue, it is attenuated differently. The use of contrast can further enable the contrast material (e.g., which may be flowing in a vein or artery) to be distinguished from surrounding tissue.

The imager 102 can be communicatively coupled to the processing module 106 and/or the display module 110 via any suitable technique, such as wired or wireless connections, including direct connections or networked connections. In some cases, imager 102 can be coupled to processing module 106 via a network, such as a local area network, a wide area network, a cloud network, or the Internet. In some cases, data transfer between the imager 102 and the processing module 106 can occur via removable physical media, such as compact disks or flash drives.

The imaging data 104 can be stored and/or transferred in any suitable format. In some cases, the imaging data 104 can be stored and/or displayed as two-dimensional or three-dimensional images. In some cases, the imaging data 104 can be stored as a collection of data points or voxels.

The processing module 106 can be any suitable computing device for processing the imaging data 104 as disclosed herein. The processing module 106 can receive the imaging data 104 and analyze the imaging data 104 to generate output data 108. The output data 108 can include any CTA-derived aortic valve parameters as disclosed herein, such as i) a calcific tissue volume; ii) a calcific tissue percentage of the total tissue volume; iii) a noncalcific tissue volume; iv) a noncalcific tissue percentage of the total tissue volume; v) a total tissue volume; or vi) any combination of i-v. In some cases, the output data 108 can further include the imaging data 104 (e.g., a two-dimensional or three-dimensional image).

In some cases, the processing module 106 can include an input device, such as a computer mouse, keyboard, touchscreen, or the like. The input device can allow a user (e.g., a physician or other medical professional) to interact with the imaging data 104 and control generation of the output data 108. In some cases, input from a user may be used to establish and/or adjust regions of interest that will be used to generate the output data 108. In some cases, the processing module 106 can include the display module 110 for displaying imaging data 104 and/or output data 108. In some cases, the display module 110 is used in conjunction with or includes an input device.

The output data 108, once generated, can be presented on the display module 110 or otherwise presented to a user or patient. The output data 108, especially CTA-derived aortic valve parameters, can be usable to assess and/or diagnose AS, differentiate HG-AS from LFLG-AS, and/or assess prognoses of a TAVI procedure outcome.

Figure 2:
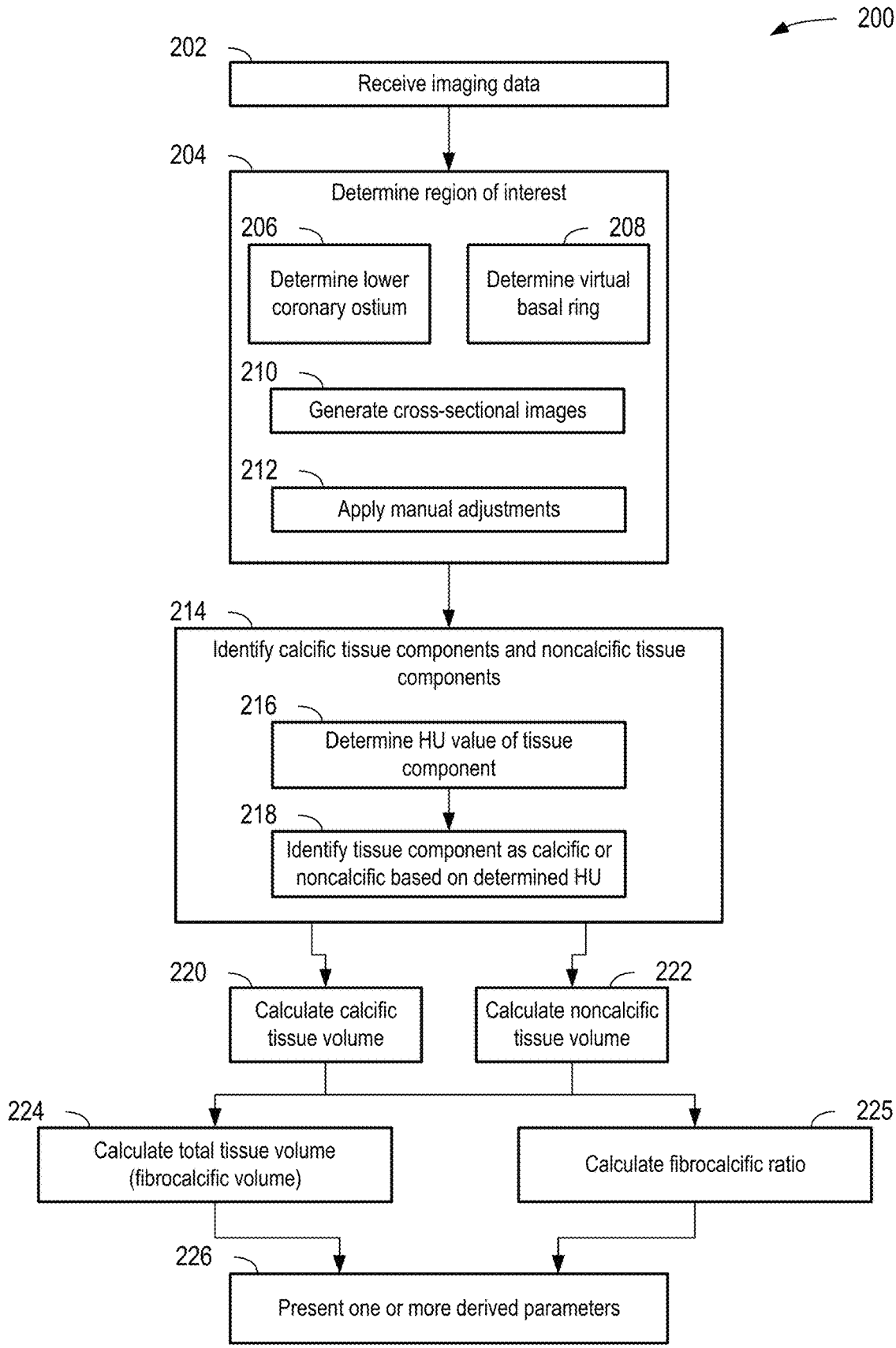
FIG. 2 is flowchart depicting a process for processing imaging data, according to certain aspects of the present disclosure.

FIG. 2 is flowchart depicting a process 200 for processing imaging data, according to certain aspects of the present disclosure. Process 200 can be used by processing module 106 of FIG. 1 to process imaging data 104 of FIG. 1.

At block 202, imaging data is received. Receiving imaging data can be received in any suitable fashion, such as by acquiring new imaging data using an imager (e.g., a CT scanner) or accessing existing imaging data from a storage device (e.g., a removable storage media or a network-accessible a database). The imaging data can be CT imaging data. In some cases, the imaging data is specifically CTA imaging data. In some cases, the imaging data is specifically non-contrast CTA imaging data.

At block 204, a region of interest is determined. The region of interest can define the valve tissue. Determining a region of interest can be manual, automatic, or semi-automatic.

Manual determination of a region of interest can include receiving user input to define the region of interest. For example, user input can be received in association with displayed projections of the imaging data. The display can present the imaging data along with one or more tools used to create, alter, or delete portions of the region of interest. Thus, a user can manually define the region of interest.

Automatic determination of a region of interest can include applying the imaging data to a machine learning algorithm that is trained to output a region of interest. Such a machine learning algorithm can be trained using labeled training data that includes manually generated regions of interest. In some cases, however, a machine learning algorithm can be trained using unsupervised or semi-supervised training.

Semi-automatic determination of a region of interest can include determining an initial region of interest and then updating the initial region of interest using manual adjustments. In some cases, an initial region of interest can be determined by first determining a lower coronary ostium at block 206, then determining a virtual basal ring at block 208. Determining the lower coronary ostium at block 206 can be automatically performed via an aortic landmark detection algorithm. Determining the virtual basal ring at block 208 can be automatically performed via an aortic landmark detection algorithm (e.g., to identify the hinges of the valve leaflets and automatically define a plane intersecting the hinges of the valve leaflets). The initial region of interest can be defined as a region between the lower coronary ostium and the virtual basal ring (e.g., the plane upon which the virtual basal ring lies). After this initial region of interest is defined, cross-sectional images of the initial region of interest can be obtained at block 210 (e.g., via rendering serial multiplanar reformatted images orthogonal to the longitudinal axis of the ascending aorta). These cross-sectional images can include contouring of the region of interest. This updated region of interest can define an approximate three dimensional region associated with the valve tissue.

At block 212, manual adjustments can be applied. In some cases, applying manual adjustments can include adjusting one or more parameters that affect how the automatic portion of the semi-automatic determination. In some cases, however, applying manual adjustments can include adjusting one or more adjustable points of the existing region of interest. In such cases, multiple adjustable points defining the region of interest can be automatically applied or manually added. Then, the adjustable points can be manually adjusted by a user, such as via an input device (e.g., a mouse controlling a cursor on a screen or a touchscreen interface), to change the boundaries of the region of interest. In some cases, the number of adjustable points that are automatically applied can be in the range of 15-20 points, although that need not always be the case. Applying manual adjustments at block 212 can continue until the region of interest covers the valve tissue.

At block 214, calcific tissue components and noncalcific tissue components can be identified. Identifying the calcific tissue components and noncalcific tissue components can include classifying the region of interest into calcific tissue, noncalcific tissue, and optionally, ignored components (e.g., non-valvular-tissue components, such as blood). Each sub-region within the region of interest can be classified. A sub-region can be a voxel or collection of voxels (e.g., adjacent voxels). At block 216, the HU value of a tissue component (e.g., a voxel within the region of interest) is determined. Determining the HU value can be performed using standard techniques to calculate HU values. At block 218, the tissue component can be identified (e.g., classified) as calcific or noncalcific (or optionally, an ignored component) based on the determined HU value from block 216.

In some cases, I identification at block 218 can be based on preset threshold values for calcific and noncalcific tissue components. Calcific tissue is identified as any tissue having a HU value at or above the calcific HU threshold (e.g., 650 HU). Noncalcific tissue is identified as any tissue having a HU value at or below the noncalcific HU threshold (e.g., 350 HU), although in some cases noncalcific tissue must also have a HU value at or above a lower noncalcific HU threshold (e.g., −30 HU).

Tissue identified as calcific or noncalcific at block 214 can be optionally presented to the user, such as via a display. Presenting the calcific or noncalcific tissue components can include displaying imaging data (e.g., two-dimensional projections from the imaging data) or a generated three-dimensional model with the calcific tissue components and noncalcific tissue components presented in a discernable fashion (e.g., visually discernable, such as presented in different colors). For example, calcific tissue components may be presented in yellow color and noncalcific tissue components may be presented in red color. Other colors or presentation techniques can be used.

In some optional cases, one or more of the HU threshold values (e.g., the calcific HU threshold, the noncalcific HU threshold, or the lower noncalcific HU threshold) can be manually adjusted, as needed. Manual adjustment can be controlled by user input, and can dynamically update presentation of the calcific and/or noncalcific tissue components. Thus, a skilled user can fine-tune the tissue classification.

In some cases, the identification at block 218 can include applying Gaussian mixture modeling to identify a tissue component as non-calcific tissue or calcific tissue, or optionally blood pool. In some cases, for non-calcific tissue, a fixed lower threshold of at or approximately 45 HU can be used to exclude artefacts (e.g., photon starvation adjacent to dense calcification). In some cases, for non-calcific tissue, an upper threshold can be set at the 0.3 percentile of the blood pool CT attenuation. For calcific tissue, a lower threshold can be set at or around 99.7 percentile of the blood pool CT attenuation and all tissue above this threshold can be considered to be calcium. To account for differences in valve size, calcific and non-calcific volumes can be indexed to the annulus area of the valve.

After the tissue components have been classified, a calcific tissue volume can be calculated at block 220 and a noncalcific tissue volume can be calculated at block 222. Calculating the calcific tissue volume at block 220 can include calculating the cumulative volume of all tissue components identified as calcific from block 214. Calculating the noncalcific tissue volume at block 222 can include calculating the cumulative volume of all tissue components identified as noncalcific from block 214. At block 224, a total tissue volume can be calculated. The total tissue volume can be the sum of the calcific and noncalcific tissue volumes. The total tissue volume can be known as a fibrocalcific volume.

In some cases, at block 225, a fibrocalcific ratio can be calculated. The fibrocalcific ratio can be calculated as the noncalcific volume divided by the calcific volume.

At block 226, one or more of the derived parameters can be presented. The derived parameters can include i) the calculated calcific tissue volume from block 220, ii) the calculated noncalcific tissue volume from block 222, iii) the calculated total tissue volume from block 224, iv) a calculated calcific tissue percentage of the total tissue volume, v) a calculated noncalcific tissue percentage of the total tissue volume, vi) the fibrocalcific ration from block 225, vii) any other parameter derived from i-vi, or viii) any combination of i-vii. When the imaging data is CTA imaging data, the derived parameters can be CTA-derived parameters.

In some cases, presenting the one or more derived parameters at block 226 can include presenting the one or more derived parameters in association with the imaging data. In such cases, the one or more derived parameters can be presented adjacent or otherwise on the same display as imaging data. The imaging data can be presented as two-dimensional projections, three-dimensional models, or in any other suitable fashion. In some cases, the imaging data can be presented with indicators distinguishing calcific tissue components from noncalcific tissue components.

While described with a particular set of blocks in a particular order, in some cases process 200 can include fewer blocks or additional blocks, in any suitable order. For example, blocks 220 and 222 can occur simultaneously or sequentially in any order. In another example, instead of or in addition to block 226, one or more of the derived parameters can be used to generate a score. The score can be an AS severity score indicative of an estimated severity of AS associated with the valve. In some cases, the score can be a valvular gradient score indicative of a likelihood that any AS associated with the valve is either HG-AS or LFLG-AS. In some cases, the score can be a prognosis score indicative of the likelihood of a MACE within a threshold number of days post-intervention. For each of these scores, one or more threshold values can be used to interpret the score and/or apply categorical labels.

In another example, process 200 can include only calculating a noncalcific tissue volume at block 222, without necessarily calculating a calcific tissue value at block 220 and/or without necessarily calculating a total tissue volume at block 224. In such cases, the noncalcific tissue volume calculated at block 222 can be used at block 226 or otherwise used.

Figure 3:
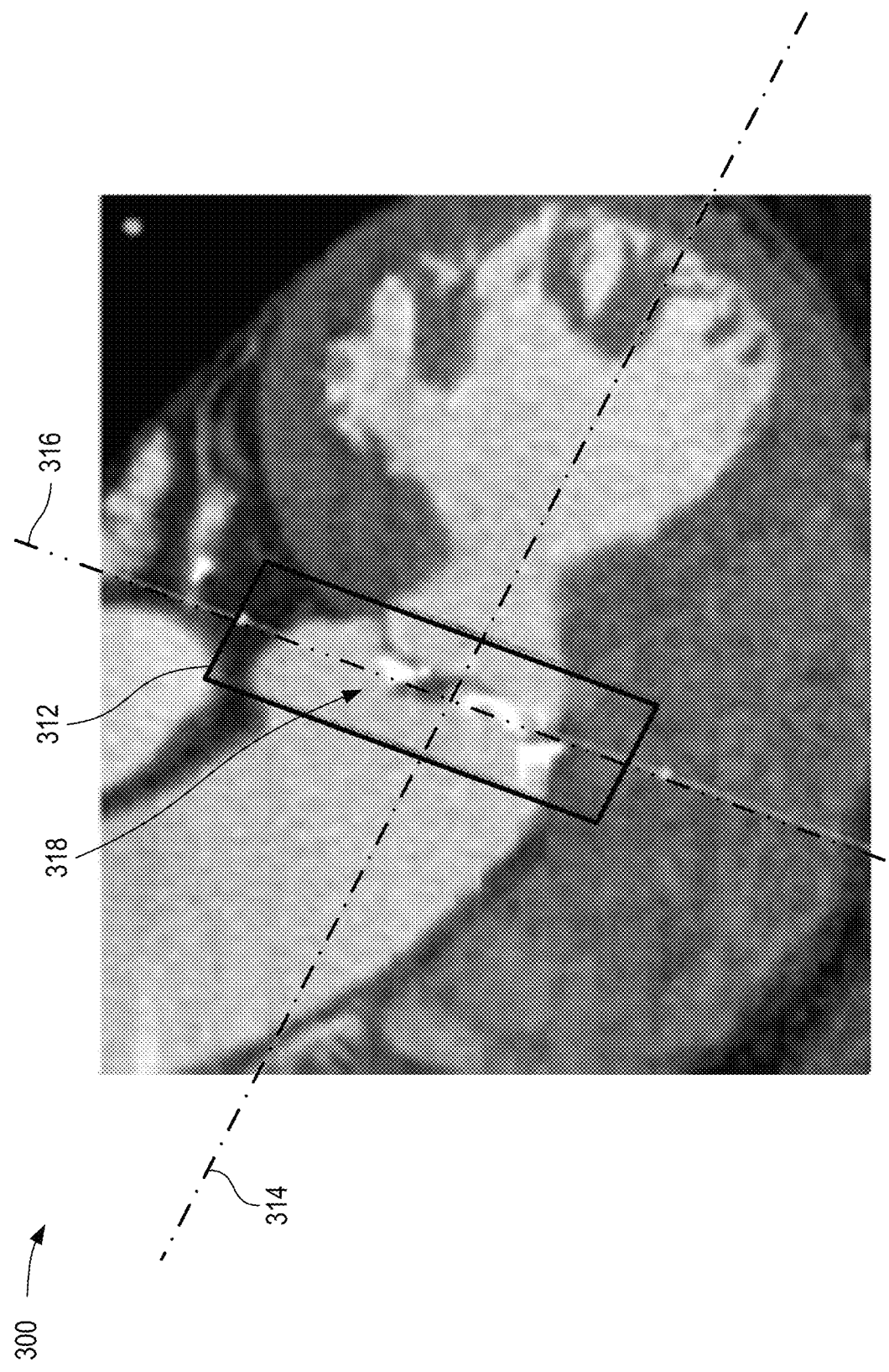
FIG. 3 is an oblique image depicting an initial region of interest around a valve, according to certain aspects of the present disclosure.

FIG. 3 is an oblique plane image 300 depicting an initial region of interest 312 around a valve 318, according to certain aspects of the present disclosure. The initial region of interest 312 can be automatically generated during semi-automatic determination of a region of interest, such as described with reference to block 204 of FIG. 2. For example, the initial region of interest 312 can be defined between the lower coronary ostium and the virtual basal ring. The virtual basal ring can be identified by the hinge points of each aortic valve cusp.

The valve 318 can rest along a valve plane 316. The initial region of interest 312 can be defined between a plane associated with the lower coronary ostium that is parallel the valve plane 316 and a plane associated with the virtual basal ring that is parallel the valve plane 316. A longitudinal axis 314 extends perpendicular to the valve plane 316, through the center of the valve 318.

Figure 4:
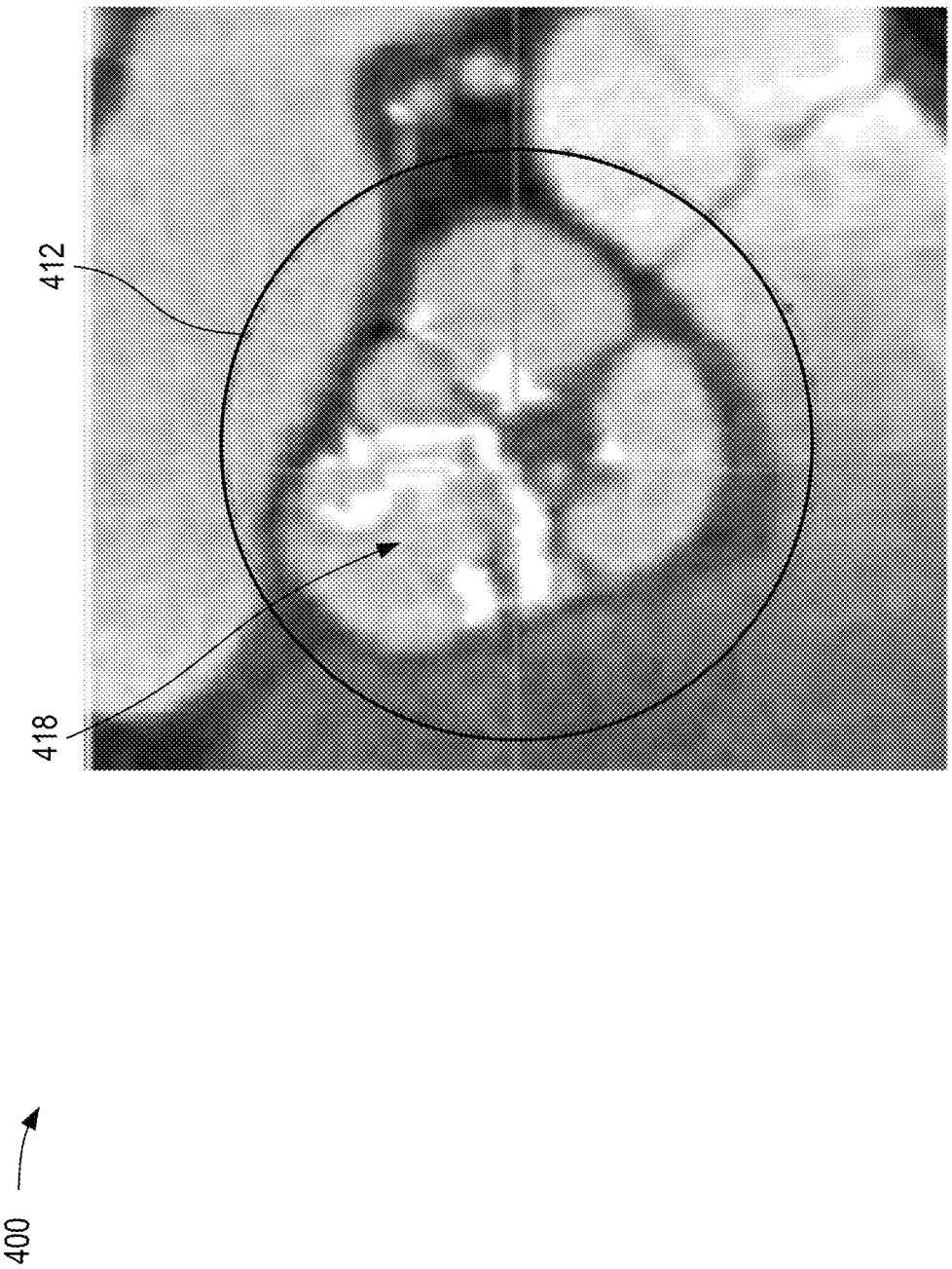
FIG. 4 is a valve plane image depicting an initial region of interest around a valve, according to certain aspects of the present disclosure.

FIG. 4 is a valve plane image 400 depicting an initial region of interest 412 around a valve 418, according to certain aspects of the present disclosure. The valve 418 can be valve 318 of FIG. 3, and the valve plane image 400 can be an image taken of a plane that is within the initial region of interest 312 of FIG. 3 and parallel to the valve plane 316 of FIG. 3.

The valve plane image 400 shows the three leaflets of the valve 418. The initial region of interest 412 can be initially defined automatically to encompass all of the three leaflets of the valve 418. In some cases, the region of interest 412 can be circular (in two-dimensions, or cylindrical in three-dimensions), although other shapes can be used.

Figure 5:
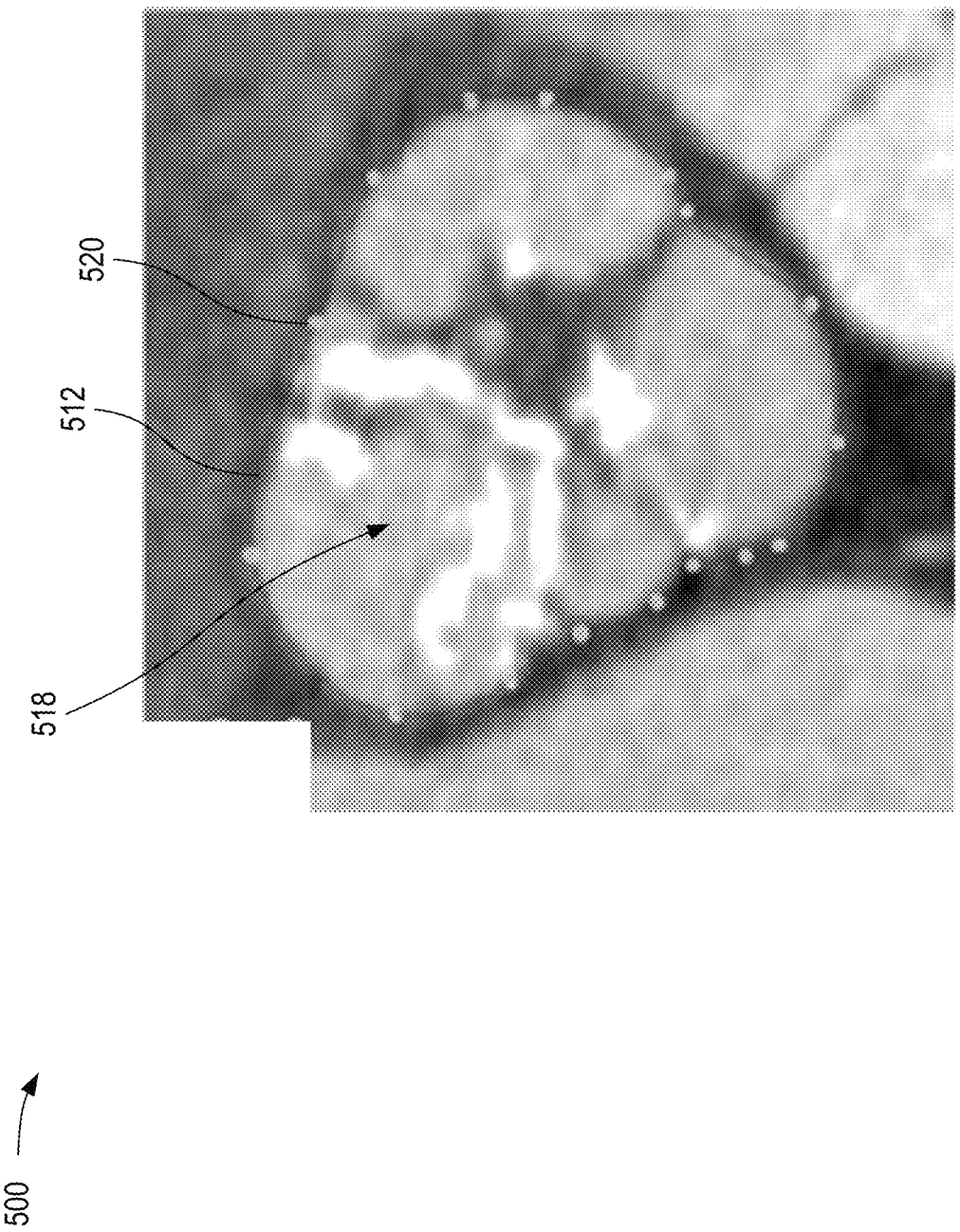
FIG. 5 is a valve plane image depicting an adjusted region of interest around a valve, according to certain aspects of the present disclosure.

FIG. 5 is a valve plane image 500 depicting an adjusted region of interest 512 around a valve 518, according to certain aspects of the present disclosure. The valve 518 can be valve 418 of FIG. 4 after the initial region of interest 412 of FIG. 4 is adjusted to the contours of the leaflets of the valve 518. Adjustment can be made manually, such as by adjusting the position of one or more adjustable points 520. Movement of an adjustable point 520 can cause the boundaries of the region of interest 512 to move. Thus, adjustment can continue until the region of interest 512 properly covers the valve 518.

Figure 6:
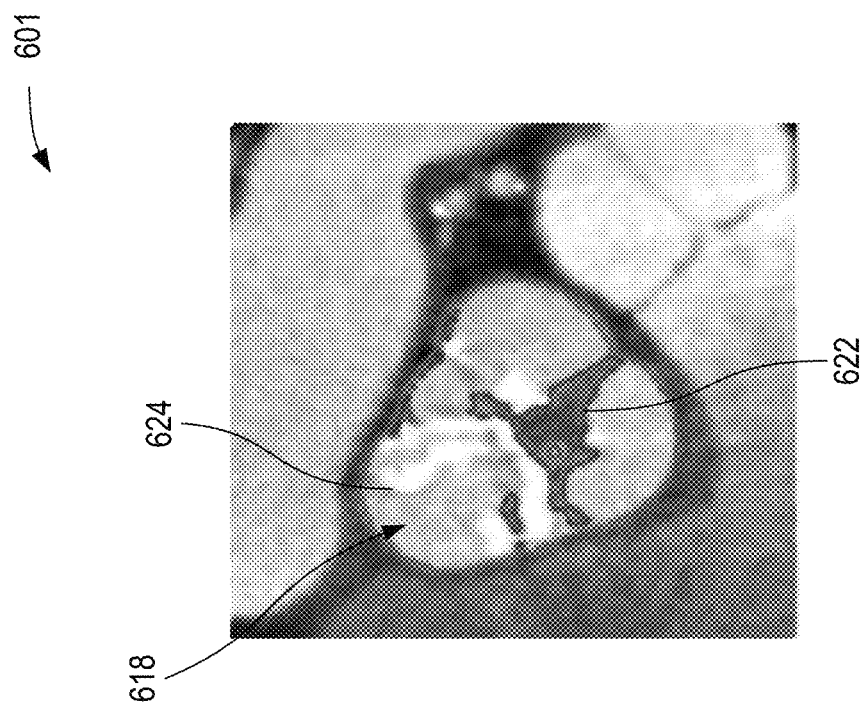
FIG. 6 is a combination oblique plane image and valve plane image depicting identified calcific and noncalcific tissue components of a valve, according to certain aspects of the present disclosure.
Figure 6:
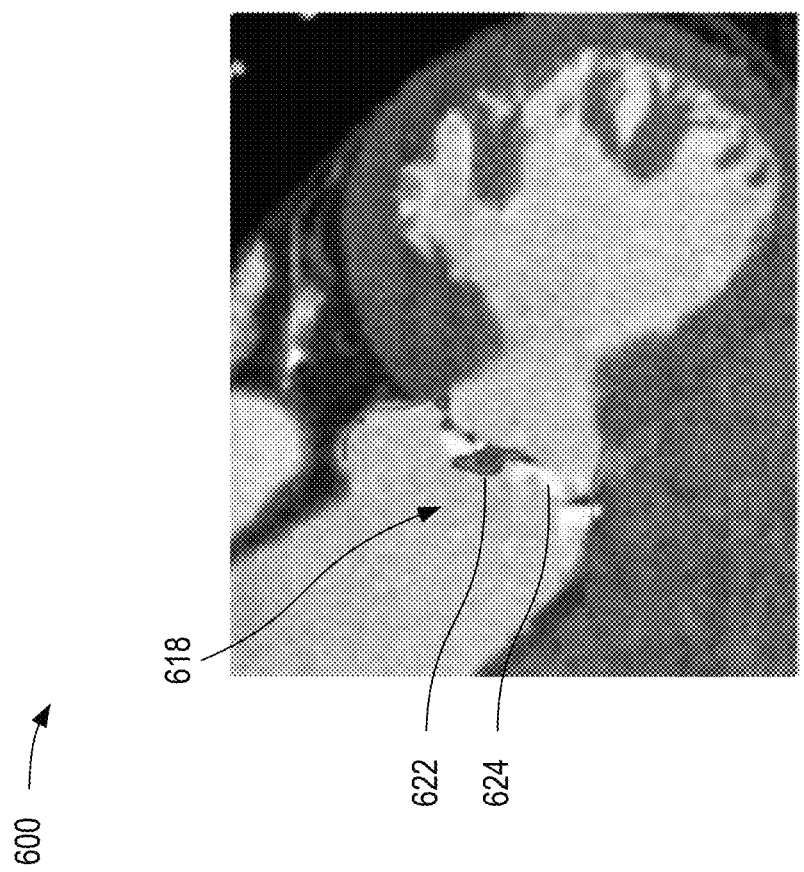

FIG. 6 is a combination image oblique plane image 600 and valve plane image 601 depicting identified calcific and noncalcific tissue components of a valve 618, according to certain aspects of the present disclosure. The valve 618 can be valve 518 of FIG. 5 after identification of calcific tissue components 624 and noncalcific tissue components 622, such as described with reference to block 214 of FIG. 2. The calcific tissue components 624 and noncalcific tissue components 622 can be identified within the region of interest (e.g., region of interest 512 of FIG. 5).

The images 600, 601 can be identical to oblique plane image 300 of FIG. 3 and valve plane image 400 of FIG. 4, respectively, but with calcific tissue components 624 and noncalcific tissue components 622 depicted in a visually distinguishable fashion. For example, calcific tissue components 624 can be highlighted in a first color (e.g., yellow) while noncalcific tissue components 622 are highlighted in a second color (e.g., red).

Figure 7:
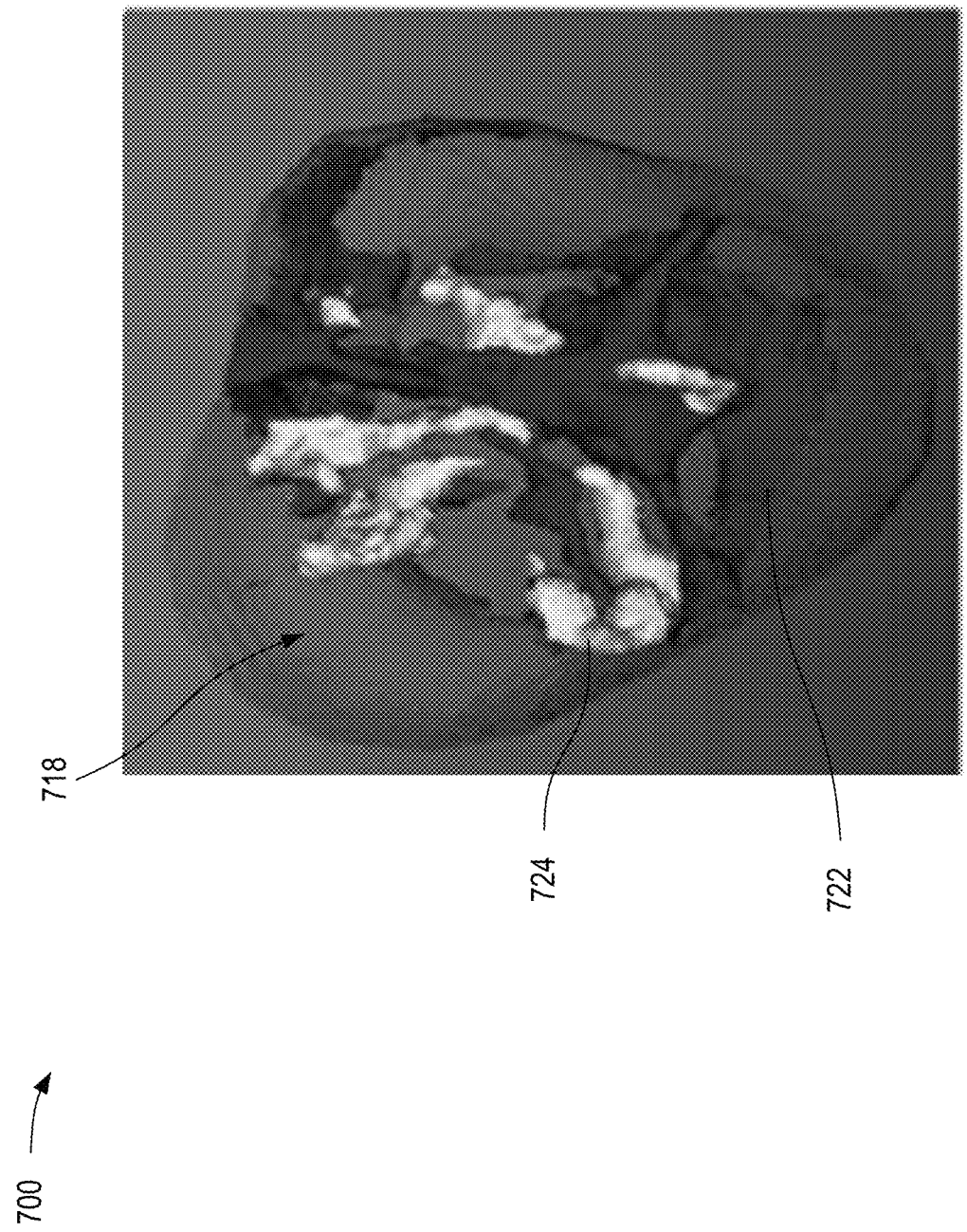
FIG. 7 is a three-dimensional model of a valve depicting identified calcific and noncalcific tissue components of the valve, according to certain aspects of the present disclosure.

FIG. 7 is a three-dimensional model 700 of a valve 718 depicting identified calcific and noncalcific tissue components of the valve 718, according to certain aspects of the present disclosure. Valve 718 can be valve 618 of FIG. 6. The three-dimensional model 700 can be generated using the image data of the region of interest (e.g., region of interest 512 of FIG. 5). The calcific tissue components 724 and noncalcific tissue components 722 can be depicted in a visually distinguishable fashion. For example, calcific tissue components 724 can be highlighted in a first color (e.g., yellow) while noncalcific tissue components 722 are highlighted in a second color (e.g., red).

FIGS. 8-14 are based on data acquired during a study applying certain aspects and features of the present disclosure. The study involved data from 447 TAVI procedures for severe calcific stenosis of a native aortic valve, which included a pre-procedural planning CTA for each procedure; and data (e.g., CTA scans for an assessment of chest pain) from a set of 224 control patients matched to the patients who underwent the TAVI procedures using gender, age, body mass index, and year of CT scan.

Pre-interventional planning CTA scans were performed on a variety of different scanner platforms using tube voltage of 100-120 kV and tube current adjusted to patients' size. The bolus-tracking technique was used, and the acquisition was triggered when the attenuation of the region of interest placed in the ascending thoracic aorta reached the threshold of 180-200 HU. During the image acquisition, 80-100 mL of iodinated contrast was injected at a rate of 3.5-5 mL/s, followed by a 30-50 mL saline chaser. Image data were reconstructed in diastole (70-80% of the R-R interval) using a soft kernel, slice thickness of 0.6 mm and an increment of 0.4 mm. In some cases, concurrent non-contrast CT scans gated from 70% to 80% of the R-R interval were performed with a tube voltage of 120 kV for CT aortic valve calcium scoring. In some cases, β-blockade was administered to achieve a resting heart rate of ≤65 beats per minute.

Quantitative analysis of aortic valve composition was based on pre-interventional planning CTA images using semi-automated software embodying certain aspects and features of the present disclosure. A standard mediastinal window (width: 400 HU; level 40 HU) was used. Calcific and noncalcific tissue volumes and tissue composition was calculated for each valve, as well as total tissue volume, according to certain aspects and features of the present disclosure. The processing time for these calculations ranged between 3 and 6 min.

Aortic valve calcium scores were calculated using a standard Agatston methodology for all available non-contrast CT scans, with a threshold for calcium detection set at 130 HU and 3-mm slice thickness.

Adjudication of AS severity for TAVI eligibility was performed by a team encompassing an experienced echocardiographer, two cardiac interventionalists, and a radiologist. Patients with symptomatic severe AS (aortic valve area <1 $cm^2$, aortic valve area indexed to body surface area <0.6 $cm^2$) were classified as HG-AS with mean transvalvular pressure gradient ≥40 mmHg or LFLG-AS with mean gradient <40 mmHg and stroke volume index <35 $mL/m^2$. Patients with LFLG-AS were further divided by their left ventricular ejection fraction (LVEF) into low-LVEF (LVEF<50%) and preserved-LVEF (LVEF≥50%). Among patients with low LVEF, LFLG-AS was distinguished from pseudo-AS with previously described criteria using transthoracic echocardiography, dobutamine stress echocardiography and cardiac CTA.

The primary outcome was a major adverse cardiovascular event (MACE) within 30 days following the procedure that included cardiovascular death, all-stroke, and myocardial infarction. All clinical events were evaluated in accordance with Valve Academic Research Consortium (VARC)-2 criteria. Any death attributable to a proximate cardiac cause or death of an unknown cause was classified as cardiac death.

Data was tested for normality using Shapiro—Wilk test. Continuous data is expressed as mean (standard deviation) or median (interquartile range (IQR)) dependent on the distribution and compared using the Student's t-test or non-parametric Mann—Whitney U-test as appropriate. Categorical variables are presented as absolute numbers (percentage) and were compared using a $\lambda^2$ test. Control patients were matched with the AS group in a 1:2 manner utilizing propensity score and a method of the nearest neighbor without replacement using gender, age, body mass index, and year of CT scan. Discriminatory performance of different aortic valve tissue composition parameters was determined by the C-statistic, and compared using the standard methods. Receiver operating characteristic (ROC) curves were generated for different aortic calcium parameters alone and their combinations with non-calcific tissue. Optimal cut-offs for tissue parameters were identified by using the Youden index. Net reclassification improvement was calculated using known methods. The correlation between two continuous variables was measured with the bivariate Pearson correlation. Multivariable logistic regression analysis was performed to evaluate the association of aortic valve composition with 30-day MACE and adjusted for common significant risk factors. The following clinical predictors were entered into backward stepwise multivariable logistic regression analysis: age, gender, diabetes mellitus, glomerular filtration rate, history of myocardial, history of stroke, LVEF, and non-femoral access site. Inter-observer variability was measured in a sample of 50 random AS patients using an interclass correlation coefficient (ICC) and Bland— Altman plots with mean bias and limits of agreement. Log-transformed values for aortic valve tissue indices were used in the statistical analyses. All probability values were two-tailed, and a P-value of <0.05 was considered statistically significant.

The study population included 447 patients, who underwent TAVI for severe AS. Mean age was 79.3±7.1 years, 211 (47.3%) of patients were males and median Logistic EuroSCORE was 7.87 (IQR 4.77-15.8). All patients were treated with second-generation transcatheter heart valves and 362 (81.0%) of patients received self-expandable valves. LFLG-AS was diagnosed in 119 (26.6%) patients: 47 (10.5%) had low and 72 (16.1%) had preserved LVEF. For the 224 control patients without known aortic valve disease, who underwent CTA for assessment of chest pain, mean age was 79.1±6.8 and 107 (47.8%) were males.

Figure 8:
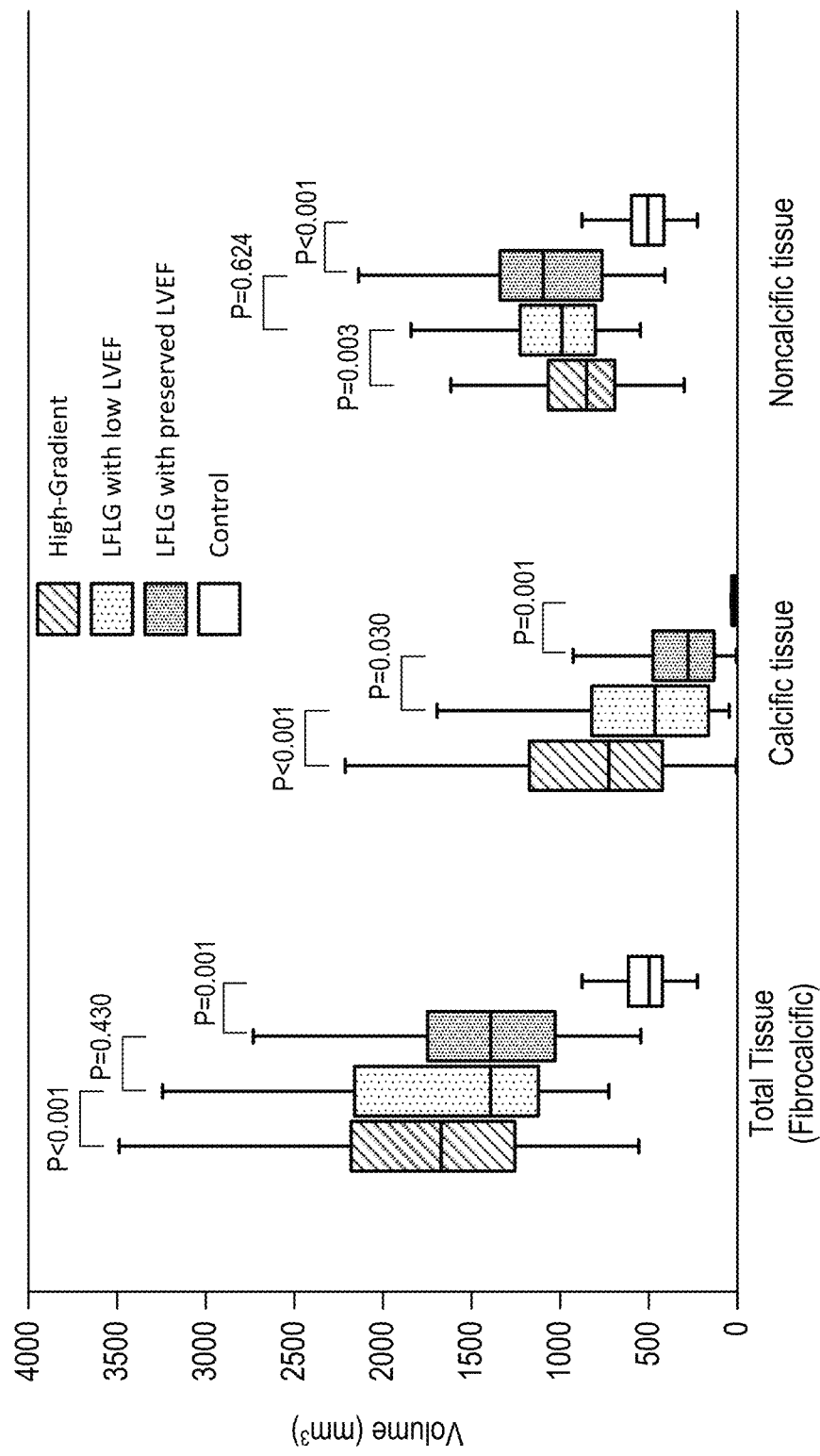
FIG. 8 is a chart depicting a comparison of tissue volumes between high-gradient aortic stenosis, low-flow low-gradient aortic stenosis, and control valves, according to certain aspects of the present disclosure.

FIG. 8 is a chart 800 depicting a comparison of tissue volumes between high-gradient aortic stenosis, low-flow low-gradient aortic stenosis, and control valves, according to certain aspects of the present disclosure.

It was determined that HG-AS patients had significantly higher aortic tissue volume compared to LFLG-AS (1672.7, IQR 1262.9-2161.5 vs. 1395.3, IQR 1062.2-1796 mm$^3$, P<0.001) patients. Volume of calcific tissue was higher in HG-AS than LFLG-AS (724.2, IQR 434.9-1165.2 vs. 328.6, IQR 143.2-619.3 mm$^3$, P<0.001), as opposed to the volume of the non-calcific that was lower in HG-AS patients compared to LFLG-AS (860.2, IQR 684.9-1067.6 vs. 1063.6, IQR 789.1-1295.6 mm$^3$, P<0.001). Tissue composition was characterized by increased calcific component in patients with HG-AS compared to LFLG-AS (45.1% vs. 26.1%, P<0.001). The proportion of the valve that was comprised of non-calcific tissue was, however, higher in LFLGAS than HG-AS (73.9% vs. 54.9% P<0.001).

Sensitivity analysis comparing the composition of aortic valve between LFLG-AS patients with low and preserved LVEF showed no significant differences in total aortic tissue volume (1395.3, IQR 1160.1-2023.0 vs. 1390.0, IQR 1035.8-1746.3 mm$^3$, P=0.430). Calcific tissue volume was lower in LFLG-AS patients with preserved LVEF than low LVEF (280.1, IQR 136.9-476.1 vs. 467.2, IQR 186.5-791.4 mm$^3$, P=0.030); however, volumes of non-calcific tissue did not significantly differ between two LFLG-AS groups (1092.1, IQR 782.1-1336.6 vs. 981.3, IQR 814.0-1210.5 mm$^3$, P=0.624).

Figure 9:
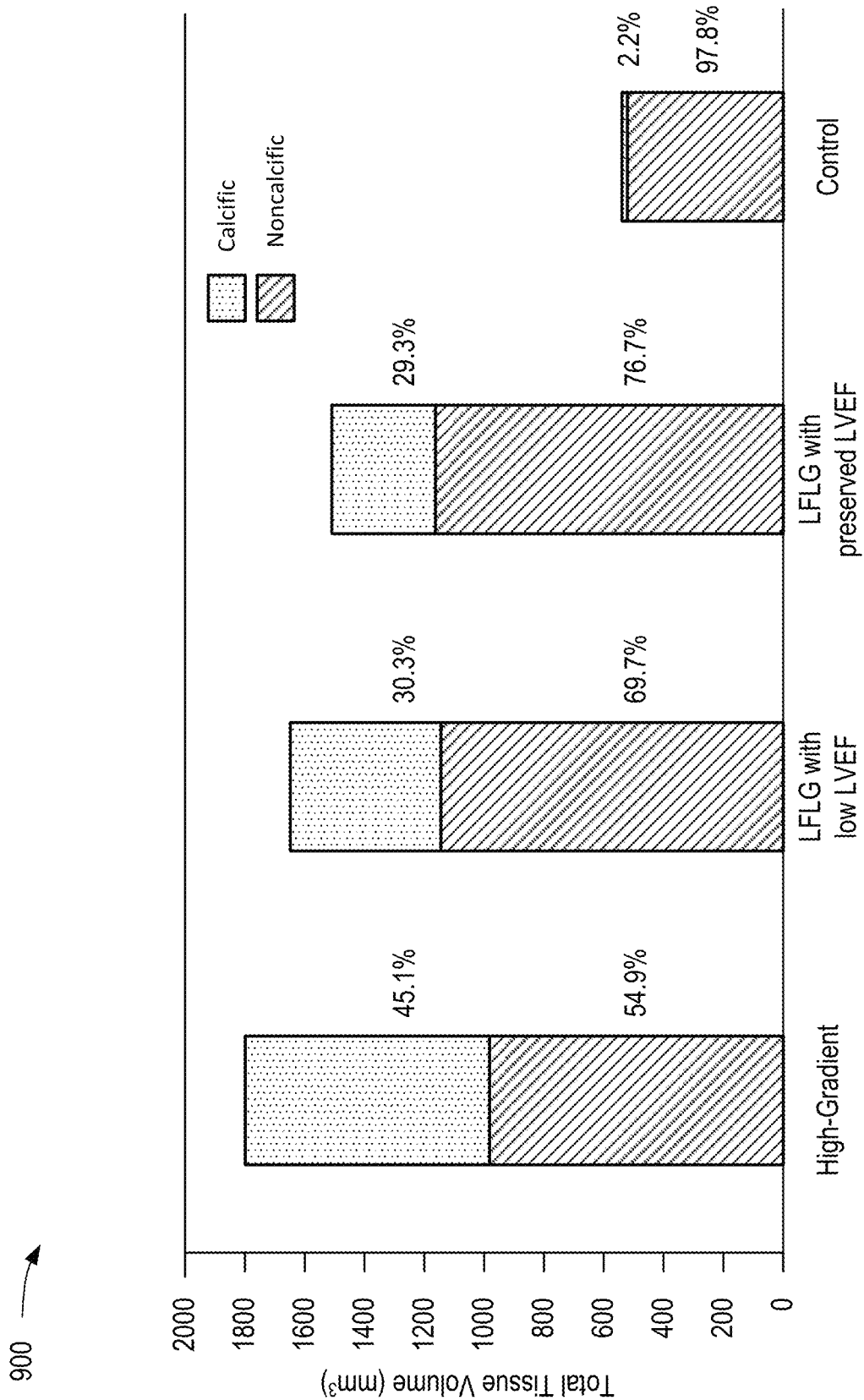
FIG. 9 is a chart depicting a comparison of tissue composition between high-gradient aortic stenosis, low-flow low-gradient aortic stenosis, and control valves, according to certain aspects of the present disclosure.

FIG. 9 is a chart 900 depicting a comparison of tissue composition between high-gradient aortic stenosis, low-flow low-gradient aortic stenosis, and control valves, according to certain aspects of the present disclosure.

Tissue composition was characterized by increased calcific component in patients with low as compared to preserved LVEF (30.3% vs. 23.3%, P=0.024).

Figure 10:
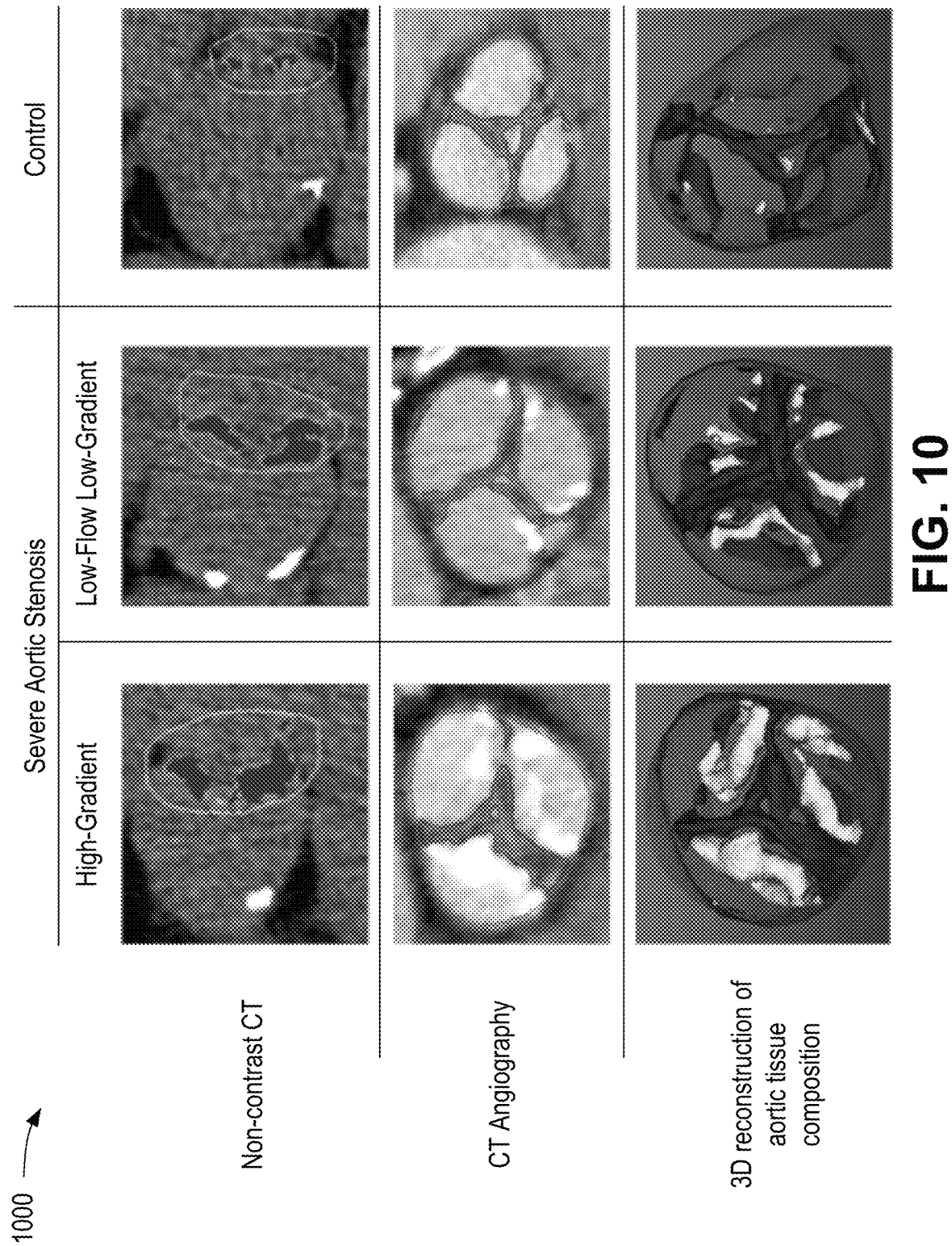
FIG. 10 is a combination image comparing non-contrast CT images, CTA images, and three-dimensional models of aortic tissue composition for different example valves, according to certain aspects of the present disclosure.

FIG. 10 is a combination image 1000 comparing non-contrast CT images, CTA images, and three-dimensional models of aortic tissue composition for different example valves, according to certain aspects of the present disclosure. The different example valves included a HG-AS valve, a LFLG-AS valve, and a control valve.

Concurrent non-contrast CT was available in 254 (56.7%) of AS and 224 (100%) control patients. Aortic valve calcium score was determined using non-contrast CT images, as indicated by the highlighted regions within the circled regions of the top three sub-images of combination image 1000. Aortic valve calcium score was significantly higher for HG-AS than LFLG-AS (3224, IQR 2284-4335 vs. 2001, IQR 1132-3354 AU, P<0.001) patients. There was very strong correlation of aortic valve calcium score with calcific tissue volume (r=0.899, P<0.001), moderate correlation with noncalcific tissue volume (r=0.616, P<0.001), and no correlation with low-attenuating tissue volume (r=0.071, P=0.123).

Figure 11:
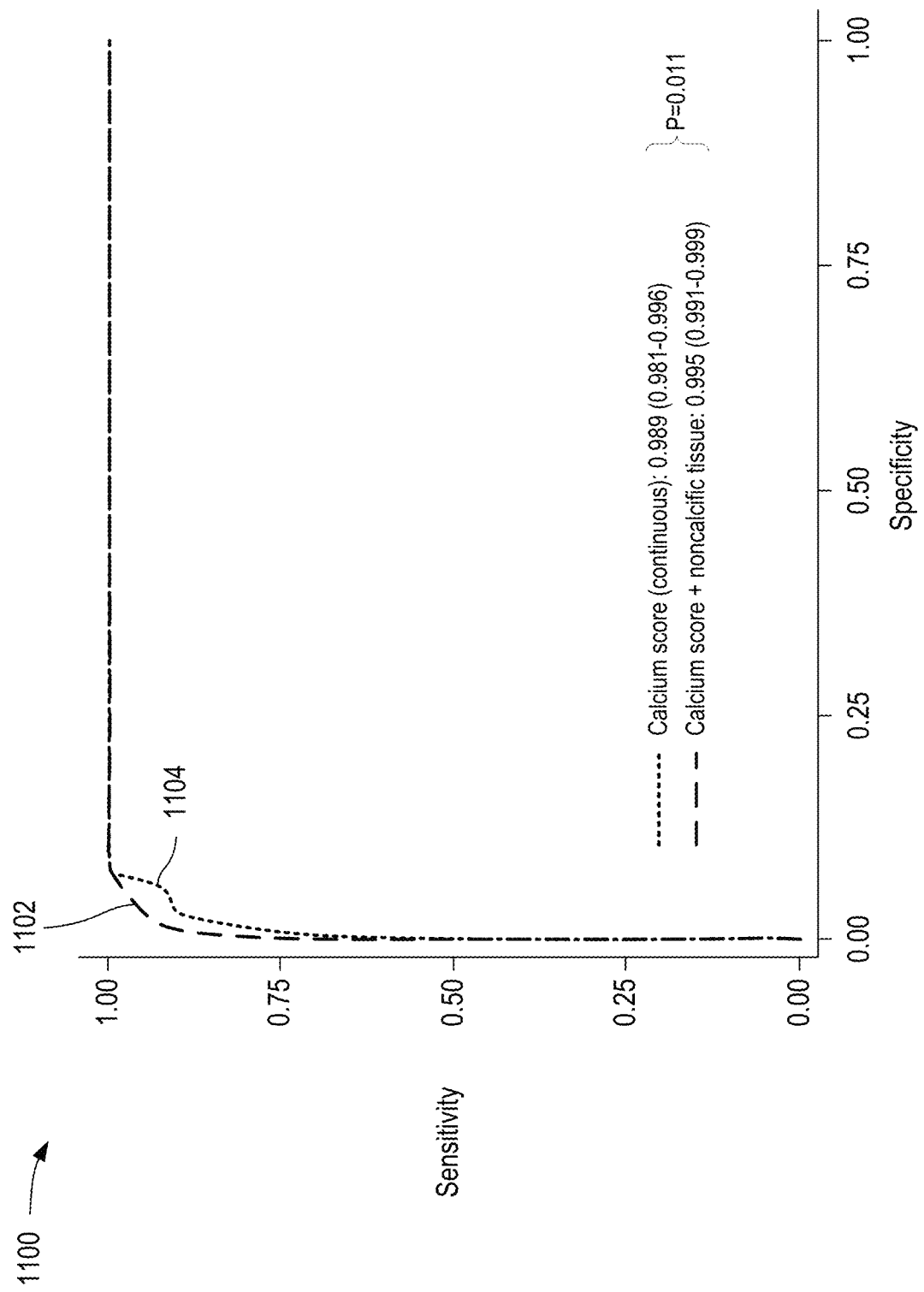
FIG. 11 is a chart depicting the additive value of non-calcific tissue volume for predicting severe aortic stenosis using aortic valve calcium measured by calcium score, according to certain aspects of the present disclosure.
Figure 12:
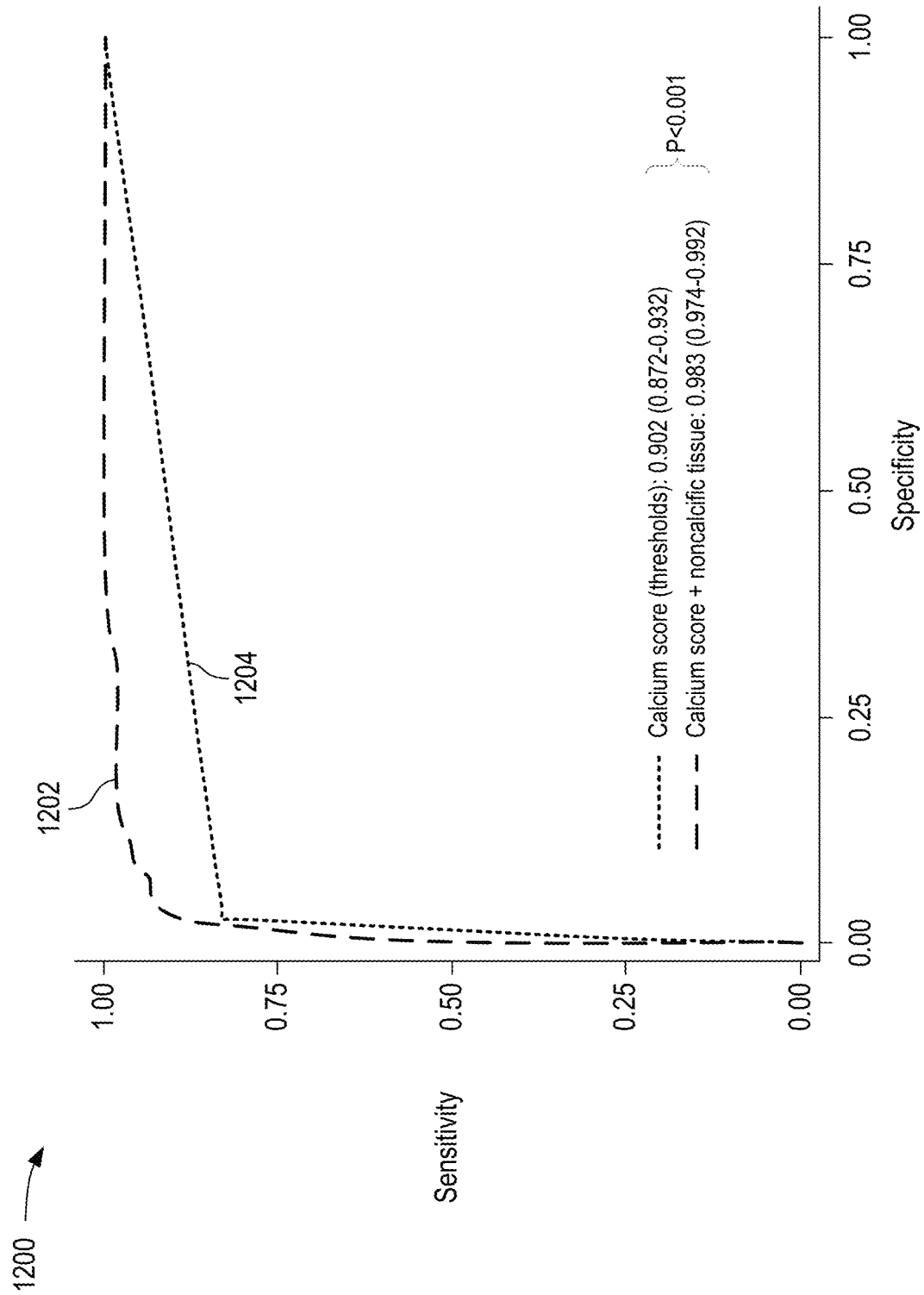
FIG. 12 is a chart depicting the additive value of non-calcific tissue volume for predicting severe aortic stenosis using aortic valve calcium measured by sex-based calcium score thresholds, according to certain aspects of the present disclosure.
Figure 13:
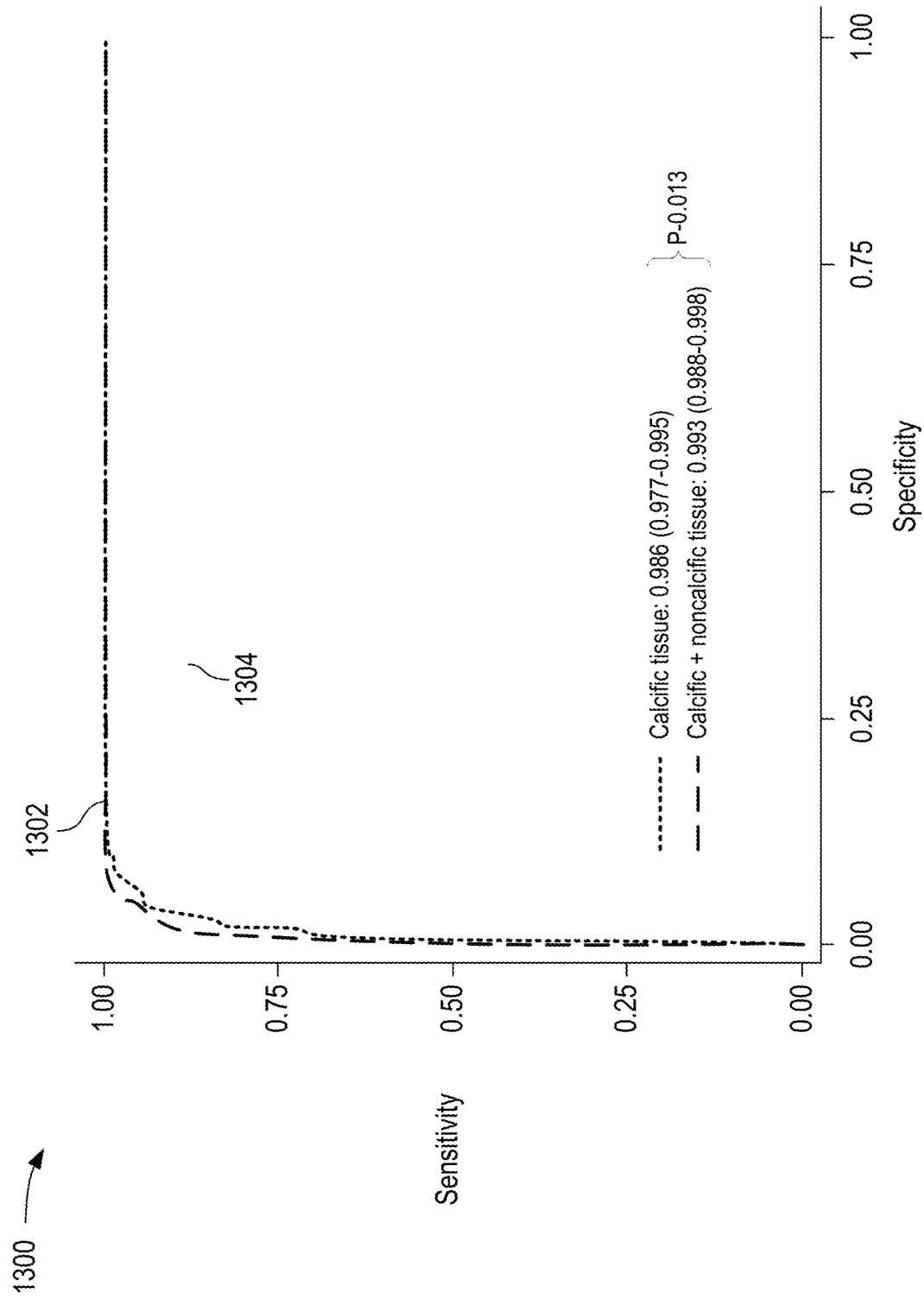
FIG. 13 is a chart depicting the additive value of non-calcific tissue volume for predicting severe aortic stenosis using aortic valve calcium measured by calcific tissue volume, according to certain aspects of the present disclosure.

FIGS. 11-13 relate to the sensitivity and specificity of different aortic tissue parameters as used to predict severe AS.

FIG. 11 is a chart 1100 depicting the additive value of non-calcific tissue volume for predicting severe aortic stenosis using aortic valve calcium measured by calcium score, according to certain aspects of the present disclosure.

FIG. 12 is a chart 1200 depicting the additive value of non-calcific tissue volume for predicting severe aortic stenosis using aortic valve calcium measured by sex-based calcium score thresholds, according to certain aspects of the present disclosure. Sex-based calcium score thresholds were 1274 AU for women and 2065 AU for men.

FIG. 13 is a chart 1300 depicting the additive value of non-calcific tissue volume for predicting severe aortic stenosis using aortic valve calcium measured by calcific tissue volume, according to certain aspects of the present disclosure.

Table 1 displays accuracy of different aortic tissue parameters for predicting severe AS, where the P-value is used to compare the area under the curve (AUC) between reference aortic valve calcium score and the different aortic valve tissue parameters derived from CTA.

TABLE 1

| Aortic tissue parameter | AUC (95% CI) | Sensitivity (95% CI) | Specificity (95% CI) | P-value |
|---|---|---|---|---|
| Aortic valve calcium score (reference) | 0.989 (0.981-0.996) | 99% (97-100%) | 93% (89-96%) | |
| Total tissue volume | 0.993 (0.988-0.998) | 98% (97-99%) | 95% (91-97%) | 0.009 |
| Calcific tissue volume | 0.986 (0.977-0.995) | 98% (96-99%) | 92% (88-95%) | 0.076 |
| Non-calcific tissue volume | 0.914 (0.893-0.935) | 79% (75-83%) | 89% (85-93%) | <0.001 |

Total tissue volume quantified from CTA presented the highest predictivity towards severe AS with an AUC of 0.993, while the AUC for non-calcific aortic tissue volume alone was 0.914. Addition of non-calcific tissue volume to calcium parameters derived from non-contrast CT as well as CTA improved significantly improved their predictive value.

Using ROC curve analysis, the optimal cut-off for non-calcific aortic tissue was >700.9 mm$^3$ (sensitivity of 83% and specificity of 92%) and for total tissue volume was >877.3 mm3 (sensitivity of 94% and specificity of 97%). Applying above noncalcific tissue volume threshold in addition to the calcium score up-classified an additional 32 (12.5%) stenotic and 17 (7.6%) control patients with a net reclassification index of 0.058 (P=0.048). Total tissue volume (representing overall valvular fibro-calcific burden) compared to the reference approach using aortic calcium score thresholds up-classified 24 (9.5%) stenotic and 1 (0.5%) control patients with a net reclassification index of 0.09 (P<0.001). Therefore, adding the new CTA measures allow correct reclassification of patients beyond traditional calcium score.

Both aortic valve calcium score and calcific tissue volume, but not non-calcific tissue volume, correlated with the different echocardiographic measures of AS severity, as seen in Table 2.

TABLE 2

|  |  | Aortic Valve Calcium Score | Total Tissue Volume | Calcific Tissue Volume | Noncalcific Tissue Volume |
|---|---|---|---|---|---|
| All Aortic Stenosis ||||||
| Aortic Valve Area | Pearson Correlation | −.603 | −.432 | −.508 | −.027 |
|  | Sig. (2-tailed) | .000 | .000 | .000 | .575 |
|  | N | 254 | 447 | 447 | 447 |
| Peak Jet Velocity | Pearson Correlation | .581 | .342 | .478 | −.104 |
|  | Sig. (2-tailed) | .000 | .000 | .000 | .029 |
|  | N | 254 | 447 | 447 | 447 |
| Mean Aortic Gradient | Pearson Correlation | .549 | .303 | .445 | −.128 |
|  | Sig. (2-tailed) | .000 | .000 | .000 | .007 |
|  | N | 254 | 447 | 447 | 447 |
| High-Gradient Aortic Stenosis ||||||
| Aortic Valve Area | Pearson Correlation | −.647 | −.432 | −.484 | −.059 |
|  | Sig. (2-tailed) | .000 | .000 | .000 | .288 |
|  | N | 189 | 328 | 328 | 328 |
| Peak Jet Velocity | Pearson Correlation | .606 | .384 | .456 | .009 |
|  | Sig. (2-tailed) | .000 | .000 | .000 | .877 |
|  | N | 189 | 328 | 328 | 328 |
| Mean Aortic Gradient | Pearson Correlation | .579 | .315 | .390 | −.020 |
|  | Sig. (2-tailed) | .000 | .000 | .000 | .713 |
|  | N | 189 | 328 | 328 | 328 |
| Low-Flow Low-Gradient Aortic Stenosis ||||||
| Aortic Valve Area | Pearson Correlation | −.337 | −.361 | −.407 | −.156 |
|  | Sig. (2-tailed) | .006 | .000 | .000 | .090 |
|  | N | 65 | 119 | 119 | 119 |
| Peak Jet Velocity | Pearson Correlation | .318 | .154 | .185 | .050 |
|  | Sig. (2-tailed) | .010 | .095 | .044 | .586 |
|  | N | 65 | 119 | 119 | 119 |
| Mean Aortic Gradient | Pearson Correlation | .313 | .201 | .203 | .122 |
|  | Sig. (2-tailed) | .011 | .028 | .027 | .187 |
|  | N | 65 | 119 | 119 | 119 |

When subdivided by type of AS, a higher correlation between tissue indices and echocardiographic parameters was found for HG-AS than LFLG-AS patients.

In the first 30 days after TAVI, MACE occurred in 28 out of 445 (6.2%) patients, who survived the procedure and there were: 16 (3.5%) cardiovascular deaths, 9 (2.0%) strokes, and 4 (0.9%) myocardial infarctions. Patients with MACE were found to have increased total volume of aortic tissue as compared to patients without such complications (2071.8, IQR 1697.2-2212.7 vs. 1588.9, IQR 1208.5-2053.2 $mm^3$, P=0.010), which was driven primarily by higher volume of non-calcific tissue (1144.9, IQR 902.7-1329.8 vs. 891.6, IQR 707.1-1137.5 $mm^3$, P<0.001).

A multivariable analysis of clinical and quantitative CT parameters of aortic valve tissue was performed for parameters such as age, male sex, diabetes mellitus, history of myocardial infarction, history of stroke, glomerular filtration rate, left ventricular ejection fraction, non-femoral access site, calcific tissue volume, and non-calcific tissue volume. It was determined that non-calcific tissue volume [odds ratio (OR) 5.2, 95% confidence interval (CI) 1.8-15.4, P=0.003] and history of stroke (OR 2.6, 95% CI 1.1-6.5, P=0.037) were independent predictors of 30-day MACE.

Figure 14:
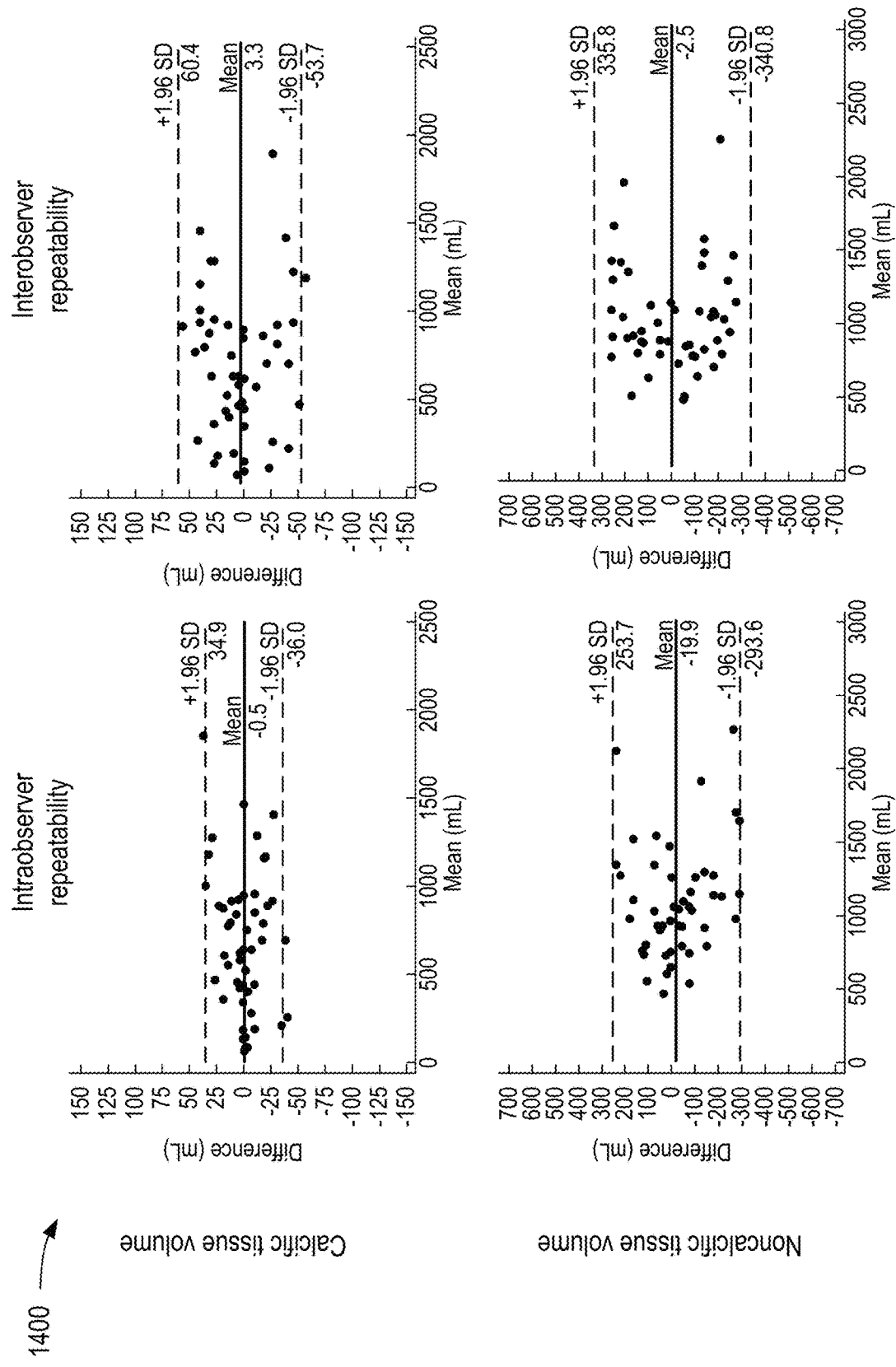
FIG. 14 is a combination chart depicting intraobserver and interobserver repeatability for calcific and noncalcific tissue volume measurements, according to certain aspects of the present disclosure.

FIG. 14 is a combination chart 1400 depicting intraobserver and interobserver repeatability for calcific and non-calcific tissue volume measurements, according to certain aspects of the present disclosure.

There was an excellent intraobserver repeatability for calcific tissue volume measurement with an ICC of 0.999, as seen in Table 3, coefficient of repeatability of 35.1, and bias of −0.5 (P=0.834).

TABLE 3

|  | Intra-observer ICC (95% CI) | P-value | Inter-observer ICC (95% CI) | P-value |
|---|---|---|---|---|
| Total tissue volume | 0.988 (0.980-0.994) | <0.001 | 0.982 (0.940-0.990) | <0.001 |
| Calcific tissue volume | 0.999 (0.998-0.999) | <0.001 | 0.998 (0.997-0.999) | <0.001 |
| Non-calcific tissue volume | 0.967 (0.942-0.981) | <0.001 | 0.945 (0.903-0.967) | <0.001 |

Similarly, intraobserver repeatability for non-calcific tissue volume was characterized with an ICC of 0.967, coefficient of repeatability of 273.8 and mean bias of −19.9 (P=0.318). Comparable to intraobserver analysis, there was also excellent interobserver repeatability for calcific tissue volume measurements with an ICC of 0.997, coefficient of repeatability of 56.8 and mean bias of 3.3 (P=0.423). Non-calcific tissue volume was characterized with an ICC of 0.945, repeatability coefficient of 334.9 and mean bias of −2.5 (P=0.918).

The use of fibrocalcific volume calculated with the use of Gaussian-mixture-modeling-based HU thresholds was studied in a set of example cases. The baseline demographics and imaging parameters of this study population are depicted in Table 4.

TABLE 4

|  | Overall | Male | Female | P value |
|---|---|---|---|---|
| Demographics |||||
| Age (years) | 72 (IQR: 68-76) | 72 (IQR: 68-76) | 72 (IQR: 67-77) | 0.73 |
| Hypertension | 104 (76%) | 82 (77%) | 22 (76%) | 0.93 |
| Diabetes Mellitus | 30 (22%) | 23 (21%) | 7 (24%) | 0.76 |
| Hypercholesterolemia | 80 (59%) | 64 (60%) | 16 (55%) | 0.65 |
| Angina | 37 (27%) | 28 (26%) | 9 (31%) | 0.61 |
| Previous Myocardial Infarction | 17 (13%) | 16 (15%) | 1 (3%) | 0.09 |
| Previous Coronary artery bypass grafting | 15 (11%) | 13 (12%) | 2 (7%) | 0.42 |

TABLE 4-continued

|  | Overall | Male | Female | P value |
|---|---|---|---|---|
| Imaging parameters at Baseline Echocardiography |  |  |  |  |
| Aortic valve Peak velocity (m/s) | 3.4 (3.0-3.8) | 3.5 (3.0-3.9) | 3.2 (2.8-3.5) | 0.02 |
| Aortic valve Mean gradient (mm Hg) | 23.8 (18.3-31.8) | 25.9 (18.9-33.0) | 21.4 (16.9-27.6) | 0.07 |
| Aortic valve area (cm$^2$) | 1.08 (0.88-1.26) | 1.02 (0.88-1.25) | 1.13 (1.00-1.28) | 0.61 |
| Stroke volume index (ml/m$^2$) | 42.0 (37.1-48.0) | 41.5 (35.8-47.0) | 44.9 (44.6-49.9) | 0.07 |
| Mild AS | 31 (23%) | 22 (20.5%) | 9 (31%) | 0.34 |
| Moderate AS | 81 (60%) | 63 (59%) | 18 (62%) | 0.92 |
| Severe AS | 24 (18%) | 22 (20.5%) | 2 (7%) | 0.15 |
| CT |  |  |  |  |
| Agatston calcium Score | 1141 (649.7-2153.3) | 1268 (760.0-2338.0) | 460 (205.5-1110.0) | <0.0001 |
| Calcific volume (mm$^3$/cm$^2$) | 51 (24.8-101.0) | 64 (36.6-122.6) | 16 (7.6-41.4) | <0.0001 |
| Non-calcific volume (mm$^3$/cm$^2$) | 156 (113.6-194.8) | 156 (114.3-194.7) | 163 (96.9-200.3) | 0.70 |
| Fibrocalcific volume (mm$^3$/cm$^2$) | 223 (172.0-271.4) | 235 (189.1-274.7) | 182 (129.3-238.9) | 0.006 |
| Fibrocalcific Ratio | 2.7 (1.2-6.0) | 2.1 (1.1-4.5) | 6.4 (2.9-16.0) | <0.0001 |

In these example cases, it was found that the use of Gaussian mixture modeling to obtain HU thresholds and then calculate fibrocalcific volume was able to track AS disease progression with time and was able to characterize changes in both the calcific and non-calcific valve burden, as depicted in Table 5. Table 5 depicts disease progression measured with contrast CT angiography, CT calcium scoring, and Echocardiography.

TABLE 5

|  | Baseline | 1 year follow-up | Percentage change (%) | Absolute change Mean (IQR) | Absolute change mean ± SD | P value |
|---|---|---|---|---|---|---|
| Indexed Non-Calcific Volume (mm$^3$/cm$^2$) | 156 (114-195) | 158 (115-205) | 8% | 12 (−7-35) | 13.1 ± 37.2 | =0.003 |
| Indexed Calcific Volume (mm$^3$/cm$^2$) | 51 (25-101) | 79 (42-139) | 37% | 16 (7-38) | 25.0 ± 31.4 | <0.0001 |
| Indexed Fibrocalcific Volume (mm$^3$/cm$^2$) | 223 (172-271) | 244 (198-305) | 17% | 32 (7-60) | 37.1 ± 37.9 | <0.0001 |
| Agatston Calcium Score | 1141 (650-2153) | 1319 (741-2398) | 22% | 214 (81-401) | 304.1 ± 363.7 | <0.0001 |
| Aortic valve peak velocity (m/s) | 3.37 (3.01-3.87) | 3.65 (3.09-4.12) | 8% | 0.27 (0.11-0.49) | 0.28 ± 0.27 | <0.0001 |
| Aortic valve mean gradient (mmHg) | 23.8 (18.3-31.8) | 27.0 (18.9-35.4) | 18% | 3.2 (−0.3-7.6) | 4.2 ± 7.2 | <0.0001 |
| Aortic valve area (cm2) | 1.08 (0.88-1.24) | 0.99 (0.80-1.17) | 9% | −0.10 (−0.17-−0.04) | −0.12 ± 0.12 | <0.0001 |

In these example cases, the fibrocalcific volume increased by 17% after 1 year, demonstrating a close association with haemodynamic progression assessed on echocardiography during the same period. Combined with its excellent scan-rescan reproducibility, these data indicate that the fibrocalcific volume is well suited to tracking disease progression in patients with aortic stenosis.

Thus, certain aspects of the present disclosure address differences in potential causes of disease progression. Both valve fibrosis and valve calcification are important in the pathogenesis and progression of aortic stenosis, and the approach of certain aspects of the present disclosure provides a measure of the impact of potential treatment interventions on both valvular fibrosis and calcification.

Additionally, certain aspects of the present disclosure address a potential sex bias in the assessment of aortic stenosis. Women develop less valvular calcification than men and appear to have a greater contribution of fibrosis. These results are consistent with the greater correlation of hemodynamic disease progression with the fibrocalcific volume than isolated measures of calcification, something which was less apparent in men.

Additionally, certain aspects of the present disclosure provide a more global assessment of disease burden in the aortic valve than existing approaches. The approaches of certain aspects of the present disclosure are arguably closer to the actual pathological disease process than echocardiography, which predominantly assesses the functional consequences of aortic valve disease. This is analogous to anatomical atherosclerotic plaque and functional ischemia assessments in coronary artery disease. Thus, anatomical assessments of disease burden (e.g., fibrocalcific burden) may represent a more sensitive and reproducible method of detecting effects of treatment interventions than the consequences for valve function (mean aortic valve gradient), albeit the latter may be more clinically important for patient management. Indeed, given its favorable reproducibility and progression data, anticipated sample sizes for studies using the fibrocalcific volume to investigate whether novel treatments impact disease progression are approximately 10-fold less than for similar studies using echocardiography.

Figure 15:
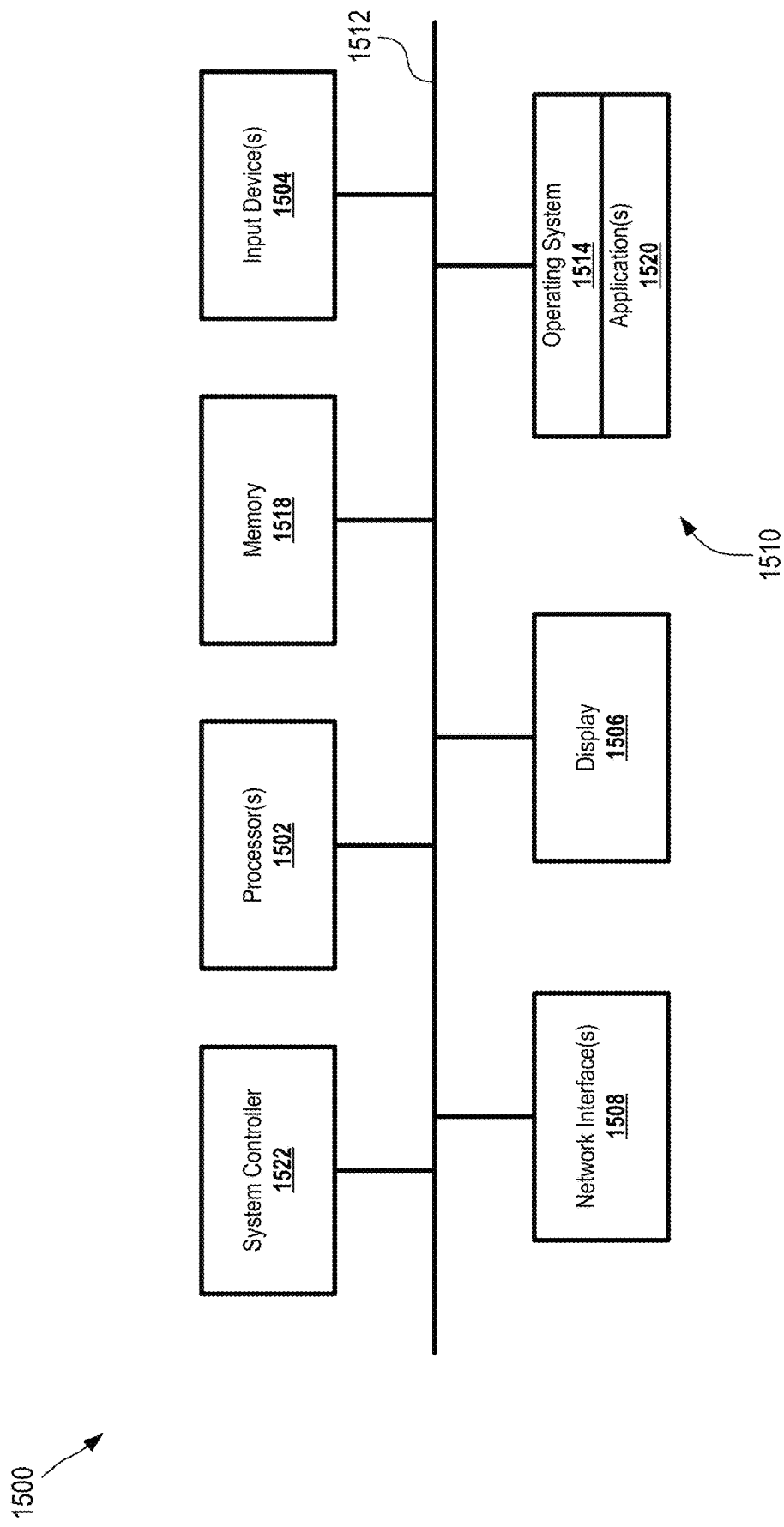
FIG. 15 is a block diagram depicting an example system architecture for implementing certain features and processes of the present disclosure.

FIG. 15 is a block diagram of an example system architecture 1500 for implementing features and processes of the present disclosure, such as those presented with reference to FIG. 2. The system architecture 1500 can be used to implement any suitable computing device (e.g., a server, workstation, tablet, CT imager, imaging data processing module, or other such device) for practicing the various features and processes of the present disclosure. The system architecture 1500 can be implemented on any electronic device that runs software applications derived from compiled instructions, including without limitation personal computers, servers, smart phones, electronic tablets, game consoles, email devices, and the like. In some implementations, the system architecture 1500 can include one or more processors 1502, one or more input devices 1504, one or more display devices 1506, one or more network interfaces 1508, and one or more computer-readable mediums 1510. Each of these components can be coupled by bus 1512.

In some cases, system architecture 1500 can be incorporated into a computing system capable of performing CT imaging, such as a computing system used to control a CT scanner or other suitable imaging equipment. In some cases, system architecture 1500 can be incorporated into a workstation computer used primarily for viewing and interpreting imaging data, such as a workstation located in the office of a medical professional interpreting the imaging data acquired at a different location (e.g., a different facility).

Display device 1506 can be any known display technology, including but not limited to display devices using Liquid Crystal Display (LCD) or Light Emitting Diode (LED) technology. Processor(s) 1502 can use any known processor technology, including but not limited to graphics processors and multi-core processors. Input device 1504 can be any known input device technology, including but not limited to a keyboard (including a virtual keyboard), mouse, track ball, and touch-sensitive pad or display. Bus 1512 can be any known internal or external bus technology, including but not limited to ISA, EISA, PCI, PCI Express, NuBus, USB, Serial ATA or FireWire.

Computer-readable medium 1510 can be any medium that participates in providing instructions to processor(s) 1502 for execution, including without limitation, non-volatile storage media (e.g., optical disks, magnetic disks, flash drives, etc.) or volatile media (e.g., SDRAM, ROM, etc.). The computer-readable medium (e.g., storage devices, mediums, and memories) can include, for example, a cable or wireless signal containing a bit stream and the like. However, when mentioned, non-transitory computer-readable storage media expressly exclude media such as energy, carrier signals, electromagnetic waves, and signals per se.

Computer-readable medium 1510 can include various instructions for implementing operating system 1514 and applications 1520 such as computer programs. The operating system can be multi-user, multiprocessing, multitasking, multithreading, real-time and the like. The operating system 1514 performs basic tasks, including but not limited to: recognizing input from input device 1504; sending output to display device 1506; keeping track of files and directories on computer-readable medium 1510; controlling peripheral devices (e.g., disk drives, printers, etc.) which can be controlled directly or through an I/O controller; and managing traffic on bus 1512. Computer-readable medium 1510 can include various instructions for implementing firmware processes, such as a BIOS. Computer-readable medium 1510 can include various instructions for implementing any of processes described herein, including at least process 200 of FIG. 2.

Memory 1518 can include high-speed random access memory and/or non-volatile memory, such as one or more magnetic disk storage devices, one or more optical storage devices, and/or flash memory (e.g., NAND, NOR). The memory 1518 (e.g., computer-readable storage devices, mediums, and memories) can include a cable or wireless signal containing a bit stream and the like. However, when mentioned, non-transitory computer-readable storage media expressly exclude media such as energy, carrier signals, electromagnetic waves, and signals per se. The memory 1518 can store an operating system, such as Darwin, RTXC, LINUX, UNIX, OS X, WINDOWS, or an embedded operating system such as VxWorks.

System controller 1522 can be a service processor that operates independently of processor 1502. In some implementations, system controller 1522 can be a baseboard management controller (BMC). For example, a BMC is a specialized service processor that monitors the physical state of a computer, network server, or other hardware device using sensors and communicating with the system administrator through an independent connection. The BMC is configured on the motherboard or main circuit board of the device to be monitored. The sensors of a BMC can measure internal physical variables such as temperature, humidity, power-supply voltage, fan speeds, communications parameters and operating system (OS) functions.

The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language (e.g., Objective-C, Java, Python), including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors or cores, of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computing system that includes a back-end component, such as a data server, or that includes a middleware component, such as an application server or an Internet server, or that includes a front-end component, such as a client computer having a graphical user interface or an Internet browser, or any combination thereof. The components of the system can be connected by any form or medium of digital data communication such as a communication network. Examples of communication networks include, e.g., a LAN, a WAN, and the computers and networks forming the Internet.

The computing system can include clients and servers. A client and server are generally remote from each other and typically interact through a network. The relationship of client and server arises by virtue of computer programs running on the respective computers and having a client-server relationship to each other.

One or more features or steps of the disclosed embodiments can be implemented using an application programming interface (API). An API can define one or more parameters that are passed between a calling application and other software code (e.g., an operating system, library routine, function) that provides a service, that provides data, or that performs an operation or a computation.

The API can be implemented as one or more calls in program code that send or receive one or more parameters through a parameter list or other structure based on a call convention defined in an API specification document. A parameter can be a constant, a key, a data structure, an object, an object class, a variable, a data type, a pointer, an array, a list, or another call. API calls and parameters can be implemented in any programming language. The programming language can define the vocabulary and calling convention that a programmer will employ to access functions supporting the API.

In some implementations, an API call can report to an application the capabilities of a device running the application, such as input capability, output capability, processing capability, power capability, communications capability, and the like.

The foregoing description of the embodiments, including illustrated embodiments, has been presented only for the purpose of illustration and description and is not intended to be exhaustive or limiting to the precise forms disclosed. Numerous modifications, adaptations, and uses thereof will be apparent to those skilled in the art. Numerous changes to the disclosed embodiments can be made in accordance with the disclosure herein, without departing from the spirit or scope of the disclosure. Thus, the breadth and scope of the present disclosure should not be limited by any of the above described embodiments.

Although certain aspects and features of the present disclosure have been illustrated and described with respect to one or more implementations, equivalent alterations and modifications will occur or be known to others skilled in the art upon the reading and understanding of this specification and the annexed drawings. In addition, while a particular feature may have been disclosed with respect to only one of several implementations, such feature may be combined with one or more other features of the other implementations as may be desired and advantageous for any given or particular application.

The terminology used herein is for the purpose of describing particular embodiments only, and is not intended to be limiting of the disclosure. As used herein, the singular forms "a," "an," and "the" are intended to include the plural forms as well, unless the context clearly indicates otherwise. Furthermore, to the extent that the terms "including," "includes," "having," "has," "with," or variants thereof, are used in either the detailed description and/or the claims, such terms are intended to be inclusive in a manner similar to the term "comprising."

As used below, any reference to a series of examples is to be understood as a reference to each of those examples disjunctively (e.g., "Examples 1-4" is to be understood as "Examples 1, 2, 3, or 4").

Example 1 is a system, comprising: one or more data processors; and a non-transitory computer-readable storage medium containing instructions which, when executed on the one or more data processors, cause the one or more data processors to perform operations including: receiving imaging data of a portion of a heart containing a valve; determining a region of interest, wherein the region of interest contains the valve; generating cross-sectional images of the region of interest based at least in part on the determined region of interest and the received imaging data; identifying both calcific tissue components and noncalcific tissue components within the region of interest based at least in part on the generated cross-sectional images; calculating a calcific tissue volume based at least in part on the calcific tissue components; calculating a noncalcific tissue volume based at least in part on the noncalcific tissue components; and calculating a fibrocalcific volume associated with the valve based at least in part on the calcific tissue volume and the noncalcific tissue volume.

Example 2 is the system of example(s) 1, wherein determining the region of interest includes: generating multiplanar reconstructions based at least in part on the imaging data; automatically detecting a lower coronary ostium associated with the valve using the multiplanar reconstructions; automatically detecting a virtual basal ring of the valve using the multiplanar reconstructions; and automatically defining the region of interest as bounded by the detected lower coronary ostium and the detected virtual basal ring. In some cases, determining the region of interest further includes: presenting the region of interest via a display device; receiving user input indicative of one or more manual adjustments to the region of interest; and updating the region of interest based on the one or more manual adjustments.

Example 3 is the system of example(s) 1, wherein identifying both calcific tissue components and noncalcific tissue components within the region of interest includes: determining Hounsfield unit (HU)_values for voxels within the region of interest; applying Gaussian mixture modeling to the HU values to determine a set of HU distributions, the set of HU distributions including a blood pool HU distribution, a calcific tissue HU distribution, and a noncalcific tissue HU distribution; determining a calcific tissue lower threshold and a noncalcific tissue upper threshold based at least in part on at least one HU distribution of the set of HU distributions; determining the calcific tissue components based at least in part on the calcific tissue lower threshold; and determining the noncalcific tissue components based at least in part on the noncalcific tissue upper threshold. In some cases, determining the noncalcific tissue components is further based at least in part on a preset noncalcific tissue lower threshold.

Example 4 is the system of example(s) 1-3, wherein generating the cross-sectional images of the region of interest include rendering, based at least in part on the imaging data, serial multiplanar images orthogonal to a longitudinal axis of an ascending aorta associated with the heart.

Example 5 is the system of example(s) 1-4, wherein identifying both the calcific tissue components and the noncalcific tissue components includes, for each tissue component within the region of interest: determining a Hounsfield unit value associated with the tissue component; identifying the tissue component as a calcific tissue component when the Hounsfield unit value exceeds a calcific tissue threshold value; and identifying the tissue component as a noncalcific tissue component when the Hounsfield unit value is below a non-calcific tissue threshold value.

Example 6 is the system of example(s) 5, wherein the calcific tissue threshold value is between 600 HU and 700 HU, and wherein the non-calcific tissue threshold value is between 300 HU and 400 HU.

Example 7 is the system of example(s) 5 or 6, wherein the calcific tissue threshold value is 650 HU, and wherein the non-calcific tissue threshold value is 350 HU.

Example 8 is the system of example(s) 1-7, further comprising a display device, wherein the operations further include: presenting the imaging data on the display device; and presenting, on the display device and in association with the imaging data, i) the calcific tissue volume; ii) a calcific tissue percentage of the fibrocalcific volume; iii) the noncalcific tissue volume; iv) a noncalcific tissue percentage of the fibrocalcific volume; v) the fibrocalcific volume; vi) a fibrocalcific ratio of calcific tissue volume to noncalcific tissue volume; or vii) any combination of i-vi.

Example 9 is the system of example(s) 1-8, wherein the operations further include generating a severe aortic stenosis score based at least in part on the noncalcific tissue volume, wherein the severe aortic stenosis score is indicative of a severity of aortic stenosis associated with the valve.

Example 10 is a computer-implemented method, comprising: receiving imaging data of a portion of a heart containing a valve; determining a region of interest, wherein the region of interest contains the valve; generating cross-sectional images of the region of interest based at least in part on the determined region of interest and the received imaging data; identifying both calcific tissue components and noncalcific tissue components within the region of interest based at least in part on the generated cross-sectional images; calculating a calcific tissue volume based at least in part on the calcific tissue components; calculating a noncalcific tissue volume based at least in part on the noncalcific tissue components; and calculating a fibrocalcific volume associated with the valve based at least in part on the calcific tissue volume and the noncalcific tissue volume.

Example 11 is the method of example(s) 10, wherein determining the region of interest includes: generating multiplanar reconstructions based at least in part on the imaging data; automatically detecting a lower coronary ostium associated with the valve using the multiplanar reconstructions; automatically detecting a virtual basal ring of the valve using the multiplanar reconstructions; and automatically defining the region of interest as bounded by the detected lower coronary ostium and the detected virtual basal ring. In some cases, determining the region of interest further includes: presenting the region of interest via a display device; receiving user input indicative of one or more manual adjustments to the region of interest; and updating the region of interest based on the one or more manual adjustments.

Example 12 is the method of example(s) 10, wherein identifying both calcific tissue components and noncalcific tissue components within the region of interest includes: determining Hounsfield unit (HU)_values for voxels within the region of interest; applying Gaussian mixture modeling to the HU values to determine a set of HU distributions, the set of HU distributions including a blood pool HU distribution, a calcific tissue HU distribution, and a noncalcific tissue HU distribution; determining a calcific tissue lower threshold and a noncalcific tissue upper threshold based at least in part on at least one HU distribution of the set of HU distributions; determining the calcific tissue components based at least in part on the calcific tissue lower threshold; and determining the noncalcific tissue components based at least in part on the noncalcific tissue upper threshold. In some cases, determining the noncalcific tissue components is further based at least in part on a preset noncalcific tissue lower threshold Example 13 is the method of example(s) 10-12, wherein generating the cross-sectional images of the region of interest include rendering, based at least in part on the imaging data, serial multiplanar images orthogonal to a longitudinal axis of an ascending aorta associated with the heart.

Example 14 is the method of example(s) 10-13, wherein identifying both the calcific tissue components and the noncalcific tissue components includes, for each tissue component within the region of interest: determining a Hounsfield unit value associated with the tissue component; identifying the tissue component as a calcific tissue component when the Hounsfield unit value exceeds a calcific tissue threshold value; and identifying the tissue component as a noncalcific tissue component when the Hounsfield unit value is below a non-calcific tissue threshold value.

Example 15 is the method of example(s) 14, wherein the calcific tissue threshold value is between 600 HU and 700 HU, and wherein the non-calcific tissue threshold value is between 300 HU and 400 HU.

Example 16 is the method of example(s) 14 or 15, wherein the calcific tissue threshold value is 650 HU, and wherein the non-calcific tissue threshold value is 350 HU.

Example 17 is the method of example(s) 10-16, further comprising: presenting the imaging data on a display device; and presenting, on the display device and in association with the imaging data, i) the calcific tissue volume; ii) a calcific tissue percentage of the fibrocalcific volume; iii) the noncalcific tissue volume; iv) a noncalcific tissue percentage of the fibrocalcific volume; v) the fibrocalcific volume; vi) a fibrocalcific ratio of calcific tissue volume to noncalcific tissue volume; or vii) any combination of i-vi.

Example 18 is the method of example(s) 10-17, further comprising generating a severe aortic stenosis score based at least in part on the noncalcific tissue volume, wherein the severe aortic stenosis score is indicative of a severity of aortic stenosis associated with the valve.

Example 19 is a computer-program product tangibly embodied in a non-transitory machine-readable storage medium, including instructions configured to cause a data processing apparatus to perform operations including: receiving imaging data of a portion of a heart containing a valve; determining a region of interest, wherein the region of interest contains the valve; generating cross-sectional images of the region of interest based at least in part on the determined region of interest and the received imaging data; identifying both calcific tissue components and noncalcific tissue components within the region of interest based at least in part on the generated cross-sectional images; calculating a calcific tissue volume based at least in part on the calcific tissue components; calculating a noncalcific tissue volume based at least in part on the noncalcific tissue components; and calculating a fibrocalcific volume associated with the valve based at least in part on the calcific tissue volume and the noncalcific tissue volume.

Example 20 is the computer-program product of example(s) 19, wherein determining the region of interest includes: generating multiplanar reconstructions based at least in part on the imaging data; automatically detecting a lower coronary ostium associated with the valve using the multiplanar reconstructions; automatically detecting a virtual basal ring of the valve using the multiplanar reconstructions; and automatically defining the region of interest as bounded by the detected lower coronary ostium and the detected virtual basal ring. In some cases, determining the region of interest further includes: presenting the region of interest via a display device; receiving user input indicative of one or more manual adjustments to the region of interest; and updating the region of interest based on the one or more manual adjustments.

Example 21 is the computer-program product of example(s) 19, wherein identifying both calcific tissue components and noncalcific tissue components within the region of interest includes: determining Hounsfield unit (HU)_values for voxels within the region of interest; applying Gaussian mixture modeling to the HU values to determine a set of HU distributions, the set of HU distributions including a blood pool HU distribution, a calcific tissue HU distribution, and a noncalcific tissue HU distribution; determining a calcific tissue lower threshold and a noncalcific tissue upper threshold based at least in part on at least one HU distribution of the set of HU distributions; determining the calcific tissue components based at least in part on the calcific tissue lower threshold; and determining the noncalcific tissue components based at least in part on the noncalcific tissue upper threshold. In some cases, determining the noncalcific tissue components is further based at least in part on a preset noncalcific tissue lower threshold.

Example 22 is the computer-program product of example(s) 19-21, wherein generating the cross-sectional images of the region of interest include rendering, based at least in part on the imaging data, serial multiplanar images orthogonal to a longitudinal axis of an ascending aorta associated with the heart.

Example 23 is the computer-program product of example(s) 19-22, wherein identifying both the calcific tissue components and the noncalcific tissue components includes, for each tissue component within the region of interest: determining a Hounsfield unit value associated with the tissue component; identifying the tissue component as a calcific tissue component when the Hounsfield unit value exceeds a calcific tissue threshold value; and identifying the tissue component as a noncalcific tissue component when the Hounsfield unit value is below a non-calcific tissue threshold value.

Example 24 is the computer-program product of example(s) 23, wherein the calcific tissue threshold value is between 600 HU and 700 HU, and wherein the non-calcific tissue threshold value is between 300 HU and 400 HU.

Example 25 is the computer-program product of example(s) 23 or 24, wherein the calcific tissue threshold value is 650 HU, and wherein the non-calcific tissue threshold value is 350 HU.

Example 26 is the computer-program product of example(s) 19-25, wherein the operations further include: presenting the imaging data on a display device; and presenting, on the display device and in association with the imaging data, i) the calcific tissue volume; ii) a calcific tissue percentage of the fibrocalcific volume; iii) the noncalcific tissue volume; iv) a noncalcific tissue percentage of the fibrocalcific volume; v) the fibrocalcific volume; vi) a fibrocalcific ratio of calcific tissue volume to noncalcific tissue volume; or vii) any combination of i-vi.

Example 27 is the computer-program product of example(s) 19-26, wherein the operations further include generating a severe aortic stenosis score based at least in part on the noncalcific tissue volume, wherein the severe aortic stenosis score is indicative of a severity of aortic stenosis associated with the valve.

What is claimed is:

1. A system, comprising:
one or more data processors; and
a non-transitory computer-readable storage medium containing instructions which, when executed on the one or more data processors, cause the one or more data processors to perform operations including:
receiving imaging data of a portion of a heart containing a valve;
determining a region of interest, wherein the region of interest contains the valve;
generating cross-sectional images of the region of interest based at least in part on the determined region of interest and the received imaging data;
identifying both calcific tissue components and noncalcific tissue components within the region of interest based at least in part on the generated cross-sectional images;
calculating a calcific tissue volume based at least in part on the calcific tissue components;
calculating a noncalcific tissue volume based at least in part on the noncalcific tissue components; and
calculating a fibrocalcific volume associated with the valve based at least in part on the calcific tissue volume and the noncalcific tissue volume.

2. The system of claim 1, wherein determining the region of interest includes:
generating multiplanar reconstructions based at least in part on the imaging data;
automatically detecting a lower coronary ostium associated with the valve using the multiplanar reconstructions;
automatically detecting a virtual basal ring of the valve using the multiplanar reconstructions; and
automatically defining the region of interest as bounded by the detected lower coronary ostium and the detected virtual basal ring.

3. The system of claim 1, wherein identifying both calcific tissue components and noncalcific tissue components within the region of interest includes:
determining Hounsfield unit (HU)_values for voxels within the region of interest;
applying Gaussian mixture modeling to the HU values to determine a set of HU distributions, the set of HU distributions including a blood pool HU distribution, a calcific tissue HU distribution, and a noncalcific tissue HU distribution;

determining a calcific tissue lower threshold and a noncalcific tissue upper threshold based at least in part on at least one HU distribution of the set of HU distributions;

determining the calcific tissue components based at least in part on the calcific tissue lower threshold; and determining the noncalcific tissue components based at least in part on the noncalcific tissue upper threshold.

4. The system of claim 3, wherein determining the noncalcific tissue components is further based at least in part on a preset noncalcific tissue lower threshold.

5. The system of claim 1, wherein generating the cross-sectional images of the region of interest include rendering, based at least in part on the imaging data, serial multiplanar images orthogonal to a longitudinal axis of an ascending aorta associated with the heart.

6. The system of claim 1, wherein identifying both the calcific tissue components and the noncalcific tissue components includes, for each tissue component within the region of interest:

determining a Hounsfield unit value associated with the tissue component;

identifying the tissue component as a calcific tissue component when the Hounsfield unit value exceeds a calcific tissue threshold value; and identifying the tissue component as a noncalcific tissue component when the Hounsfield unit value is below a non-calcific tissue threshold value.

7. The system of claim 6, wherein the calcific tissue threshold value is between 600 HU and 700 HU, and wherein the non-calcific tissue threshold value is between 300 HU and 400 HU.

8. The system of claim 1, further comprising a display device, wherein the operations further include:

presenting the imaging data on the display device; and presenting, on the display device and in association with the imaging data, i) the calcific tissue volume; ii) a calcific tissue percentage of the fibrocalcific volume; iii) the noncalcific tissue volume; iv) a noncalcific tissue percentage of the fibrocalcific volume; v) the fibrocalcific volume; vi) a fibrocalcific ratio of calcific tissue volume to noncalcific tissue volume; or vii) any combination of i-vi.

9. The system of claim 1, wherein the operations further include generating a severe aortic stenosis score based at least in part on the noncalcific tissue volume, wherein the severe aortic stenosis score is indicative of a severity of aortic stenosis associated with the valve.

10. A computer-implemented method, comprising:

receiving imaging data of a portion of a heart containing a valve;

determining a region of interest, wherein the region of interest contains the valve;

generating cross-sectional images of the region of interest based at least in part on the determined region of interest and the received imaging data;

identifying both calcific tissue components and noncalcific tissue components within the region of interest based at least in part on the generated cross-sectional images;

calculating a calcific tissue volume based at least in part on the calcific tissue components;

calculating a noncalcific tissue volume based at least in part on the noncalcific tissue components; and calculating a fibrocalcific volume associated with the valve based at least in part on the calcific tissue volume and the noncalcific tissue volume.

11. The method of claim 10, wherein determining the region of interest includes:

generating multiplanar reconstructions based at least in part on the imaging data;

automatically detecting a lower coronary ostium associated with the valve using the multiplanar reconstructions;

automatically detecting a virtual basal ring of the valve using the multiplanar reconstructions; and automatically defining the region of interest as bounded by the detected lower coronary ostium and the detected virtual basal ring.

12. The method of claim 10, wherein identifying both calcific tissue components and noncalcific tissue components within the region of interest includes:

determining Hounsfield unit (HU)_values for voxels within the region of interest;

applying Gaussian mixture modeling to the HU values to determine a set of HU distributions, the set of HU distributions including a blood pool HU distribution, a calcific tissue HU distribution, and a noncalcific tissue HU distribution;

determining a calcific tissue lower threshold and a noncalcific tissue upper threshold based at least in part on at least one HU distribution of the set of HU distributions;

determining the calcific tissue components based at least in part on the calcific tissue lower threshold; and determining the noncalcific tissue components based at least in part on the noncalcific tissue upper threshold.

13. The method of claim 12, wherein determining the noncalcific tissue components is further based at least in part on a preset noncalcific tissue lower threshold.

14. The method of claim 10, wherein generating the cross-sectional images of the region of interest include rendering, based at least in part on the imaging data, serial multiplanar images orthogonal to a longitudinal axis of an ascending aorta associated with the heart.

15. The method of claim 10, wherein identifying both the calcific tissue components and the noncalcific tissue components includes, for each tissue component within the region of interest:

determining a Hounsfield unit value associated with the tissue component;

identifying the tissue component as a calcific tissue component when the Hounsfield unit value exceeds a calcific tissue threshold value; and identifying the tissue component as a noncalcific tissue component when the Hounsfield unit value is below a non-calcific tissue threshold value.

16. The method of claim 15, wherein the calcific tissue threshold value is between 600 HU and 700 HU, and wherein the non-calcific tissue threshold value is between 300 HU and 400 HU.

17. The method of claim 10, further comprising:

presenting the imaging data on a display device; and presenting, on the display device and in association with the imaging data, i) the calcific tissue volume; ii) a calcific tissue percentage of the fibrocalcific volume; iii) the noncalcific tissue volume; iv) a noncalcific tissue percentage of the fibrocalcific volume; v) the fibrocalcific volume; vi) a fibrocalcific ratio of calcific tissue volume to noncalcific tissue volume; or vii) any combination of i-vi.

18. The method of claim 10, further comprising generating a severe aortic stenosis score based at least in part on the noncalcific tissue volume, wherein the severe aortic stenosis score is indicative of a severity of aortic stenosis associated with the valve.

19. A computer-program product tangibly embodied in a non-transitory machine-readable storage medium, including instructions configured to cause a data processing apparatus to perform operations including:
receiving imaging data of a portion of a heart containing a valve;
determining a region of interest, wherein the region of interest contains the valve;
generating cross-sectional images of the region of interest based at least in part on the determined region of interest and the received imaging data;
identifying both calcific tissue components and noncalcific tissue components within the region of interest based at least in part on the generated cross-sectional images;
calculating a calcific tissue volume based at least in part on the calcific tissue components;
calculating a noncalcific tissue volume based at least in part on the noncalcific tissue components; and
calculating a fibrocalcific volume associated with the valve based at least in part on the calcific tissue volume and the noncalcific tissue volume.

20. The computer-program product of claim 19, wherein determining the region of interest includes:
generating multiplanar reconstructions based at least in part on the imaging data;
automatically detecting a lower coronary ostium associated with the valve using the multiplanar reconstructions;
automatically detecting a virtual basal ring of the valve using the multiplanar reconstructions; and
automatically defining the region of interest as bounded by the detected lower coronary ostium and the detected virtual basal ring.

21. The computer-program product of claim 19, wherein identifying both calcific tissue components and noncalcific tissue components within the region of interest includes:
determining Hounsfield unit (HU)_values for voxels within the region of interest;
applying Gaussian mixture modeling to the HU values to determine a set of HU distributions, the set of HU distributions including a blood pool HU distribution, a calcific tissue HU distribution, and a noncalcific tissue HU distribution;
determining a calcific tissue lower threshold and a noncalcific tissue upper threshold based at least in part on at least one HU distribution of the set of HU distributions;
determining the calcific tissue components based at least in part on the calcific tissue lower threshold; and
determining the noncalcific tissue components based at least in part on the noncalcific tissue upper threshold.

22. The computer-program product of claim 19, wherein determining the noncalcific tissue components is further based at least in part on a preset noncalcific tissue lower threshold.

23. The computer-program product of claim 19, wherein generating the cross-sectional images of the region of interest include rendering, based at least in part on the imaging data, serial multiplanar images orthogonal to a longitudinal axis of an ascending aorta associated with the heart.

24. The computer-program product of claim 19, wherein identifying both the calcific tissue components and the noncalcific tissue components includes, for each tissue component within the region of interest:
determining a Hounsfield unit value associated with the tissue component;
identifying the tissue component as a calcific tissue component when the Hounsfield unit value exceeds a calcific tissue threshold value; and
identifying the tissue component as a noncalcific tissue component when the Hounsfield unit value is below a non-calcific tissue threshold value.

25. The computer-program product of claim 24, wherein the calcific tissue threshold value is between 600 HU and 700 HU, and wherein the non-calcific tissue threshold value is between 300 HU and 400 HU.

26. The computer-program product of claim 19, wherein the operations further include:
presenting the imaging data on a display device; and
presenting, on the display device and in association with the imaging data, i) the calcific tissue volume; ii) a calcific tissue percentage of the fibrocalcific volume; iii) the noncalcific tissue volume; iv) a noncalcific tissue percentage of the fibrocalcific volume; v) the fibrocalcific volume; vi) a fibrocalcific ratio of calcific tissue volume to noncalcific tissue volume; or vii) any combination of i-vi.

27. The computer-program product of claim 19, wherein the operations further include generating a severe aortic stenosis score based at least in part on the noncalcific tissue volume, wherein the severe aortic stenosis score is indicative of a severity of aortic stenosis associated with the valve.

* * * * *

UNITED STATES PATENT AND TRADEMARK OFFICE
CERTIFICATE OF CORRECTION

PATENT NO. : 12,376,814 B2
APPLICATION NO. : 17/993819
DATED : August 5, 2025
INVENTOR(S) : Dey et al.

Page 1 of 1

It is certified that error appears in the above-identified patent and that said Letters Patent is hereby corrected as shown below:

In the Specification

At Column 1, Lines 17-19, under the heading STATEMENT REGARDING FEDERALLY SPONSORED RESEARCH OR DEVELOPMENT:
"This invention was made with government support under Grant Number HL148787 RO1, awarded by National Institutes of Health. The Government has certain rights in the invention."

Should be replaced with:
— This invention was made with government support under Grant Numbers HL148787 and HL133616, awarded by the National Institutes of Health. The Government has certain rights in the invention. —

Signed and Sealed this
Tenth Day of February, 2026

John A. Squires
*Director of the United States Patent and Trademark Office*